United States Patent [19]
Lee et al.

[11] Patent Number: 6,027,742
[45] Date of Patent: Feb. 22, 2000

[54] BIORESORBABLE CERAMIC COMPOSITES

[75] Inventors: Dosuk D. Lee, Brookline, Mass.; Christian Rey, Castanet, France; Maria Aiolova, Brookline, Mass.

[73] Assignee: Etex Corporation, Cambridge, Mass.

[21] Appl. No.: 08/732,016

[22] Filed: Oct. 16, 1996

Related U.S. Application Data

[63] Continuation-in-part of application No. 08/650,764, May 20, 1996, which is a continuation-in-part of application No. 08/446,182, May 19, 1995, Pat. No. 5,650,176.

[51] Int. Cl.$^7$ ...................................................... A61K 9/16
[52] U.S. Cl. ............................ 424/422; 424/57; 424/423; 424/426; 424/602; 423/308; 433/180
[58] Field of Search ...................... 424/400, 602, 424/603, 57, 422, 423, 426; 523/218, 219; 428/404; 423/308, 311, 312, 314, 315; 433/180, 201.1; 604/890.1; 106/690, 691, 696

[56] References Cited

U.S. PATENT DOCUMENTS

| | | |
|---|---|---|
| Re. 33,161 | 2/1990 | Brown et al. .............................. 423/308 |
| Re. 33,221 | 5/1990 | Brown et al. .............................. 423/308 |
| 4,157,378 | 6/1979 | Tomlinson et al. ...................... 423/301 |
| 4,429,691 | 2/1984 | Niwa et al. . |
| 4,612,053 | 9/1986 | Brown et al. .............................. 706/35 |
| 4,737,411 | 4/1988 | Graves, Jr. et al. ...................... 428/403 |
| 4,849,193 | 7/1989 | Palmer et al. ............................. 423/308 |
| 4,880,610 | 11/1989 | Constantz ................................. 423/305 |
| 4,917,702 | 4/1990 | Scheicher et al. .......................... 623/16 |
| 4,939,938 | 7/1990 | Ewers et al. .............................. 423/308 |
| 4,959,104 | 9/1990 | Iino et al. .................................. 106/85 |
| 5,034,059 | 7/1991 | Constantz ................................. 106/161 |
| 5,037,639 | 8/1991 | Tung .......................................... 424/57 |
| 5,047,031 | 9/1991 | Constantz ................................. 606/77 |
| 5,053,212 | 10/1991 | Constantz et al. ....................... 423/305 |
| 5,085,861 | 2/1992 | Gerhart et al. ......................... 424/78.17 |
| 5,129,905 | 7/1992 | Constantz ................................. 606/76 |
| 5,149,368 | 9/1992 | Liu et al. ................................. 424/602 |

(List continued on next page.)

FOREIGN PATENT DOCUMENTS

| | | |
|---|---|---|
| 0 347 028 | 4/1989 | European Pat. Off. . |
| 0664133 | 2/1994 | European Pat. Off. . |
| 63-170205 | 7/1988 | Japan . |
| 2182261 | 7/1990 | Japan . |
| 405305134 | 11/1993 | Japan . |
| WO 92/02453 | 7/1991 | WIPO . |
| WO 94/04657 | 8/1993 | WIPO . |
| WO 94/02412 | 7/1995 | WIPO . |
| WO 96/36562 | 5/1996 | WIPO . |
| WO 95/08319 | 11/1996 | WIPO . |
| WO 97/17285 | 11/1996 | WIPO . |

OTHER PUBLICATIONS

Abboudi et al., "Development of Organic and Polymer Carriers for Demineralized Bone Matrix: Effect of Bone Cell Behavior," Fifth World Biomaterials Congress, May 29–Jun. 2, 1996, Toronto, Canada.

Aoki, "Science and medical applications of hydroxyapatite", JAAS, pp. 11–15, 1991.

Attawia et al., "The Long Term Osteoblast Response to Poly(anhydride–co–imides): A New Degradable Polymer for Use in Bone," Fifth World Biomaterials Congress, May 29–Jun. 2, 1996, Toronto, Canada.

(List continued on next page.)

*Primary Examiner*—Neil S. Levy
*Attorney, Agent, or Firm*—Clark & Elbing LLP

[57] ABSTRACT

A composite material is provided including a strongly bioresorbable, poorly crystalline apatitic calcium phosphate composite and a supplementary material. The poorly crystalline apatitic calcium phosphate is characterized in that, when placed in an intramuscular or subcutaneous site, resorption of at least 1 g of the material is complete within one year. The supplementary material is in intimate contact with the hydroxyapatite material in an amount effective to impart a selected characteristic to the composite. The supplemental material may be biocompatible, bioresorbable or non-resorbable.

32 Claims, 9 Drawing Sheets

U.S. PATENT DOCUMENTS

| | | |
|---|---|---|
| 5,152,836 | 10/1992 | Hirano et al. . |
| 5,164,187 | 11/1992 | Constantz et al. ..................... 424/423 |
| 5,178,845 | 1/1993 | Constantz et al. ..................... 423/305 |
| 5,262,166 | 11/1993 | Liu et al. . |
| 5,279,831 | 1/1994 | Constantz et al. ..................... 424/423 |
| 5,281,265 | 1/1994 | Liu . |
| 5,286,763 | 2/1994 | Gerhart et al. . |
| 5,336,264 | 8/1994 | Constantz et al. ....................... 623/16 |
| 5,342,441 | 8/1994 | Mandai et al. . |
| 5,352,715 | 10/1994 | Wallace et al. . |
| 5,427,754 | 6/1995 | Nagata et al. . |
| 5,470,803 | 11/1995 | Bonfield et al. ............................ 501/1 |
| 5,496,399 | 3/1996 | Ison et al. .................................. 106/35 |
| 5,516,532 | 5/1996 | Atala et al. . |
| 5,522,893 | 6/1996 | Chow et al. ............................. 623/11 |
| 5,525,148 | 6/1996 | Chow et al. ............................. 106/35 |
| 5,542,973 | 8/1996 | Chow et al. ............................. 106/35 |
| 5,545,254 | 8/1996 | Chow et al. ............................. 106/35 |
| 5,665,120 | 9/1997 | Ohtsuka et al. . |
| 5,700,289 | 12/1997 | Breitbart et al. . |
| 5,782,971 | 7/1998 | Constantz et al. . |

OTHER PUBLICATIONS

Barton et al., "Surface and bulk properties of amorphous calcium phosphate" Colloid Interface Sci. [Proc. Int. Conf.], 50th 3:71 (1976) [CA 87:73954v] (Abstract).

Besic et al., "Electron probe microanalysis of noncarious enamel and dentin and calcified tissues in mottled teeth", J. Dent. Res., 48:131, (1969).

Constantz et al., "Skeletal repair by in situ formation of the mineral phase of bone", Science, 267: 1976 (1995).

Ducheyne et al., "Bioceramic Composites", Chapter 15 from An Introduction to Bioceramics, Advanced Series in Ceramics, vol. 1.

Eanes et al., "Intermediate states in the precipitation of hydroxyapatite", Nature, 208: 365–367 (1965).

Eanes et al., "Intermediate phases in the basic solution preparation of alkaline earth phosphates" Calcified Tissue Res., 2(1):38 (1968) [CA 69:110373f] (Abstract).

Eanes, "Thermochemical studies on amorphous calcium phsophate", Calc. Tiss. Res., 5:133, 1970.

Fenner et al., "High Strength Partially Absorbable Composites Produced by Sintering Method for Internal Bone Fixation," Fifth World Biomaterials Congress, May 29–Jun.2, 1996, Toronto, Canada.

Gao, T.J. "Established competence of Bioactive Composite Bone Substitute on the Healing of Diaphyseal Segmental Defects in Sheep," Fifth World Biomaterials Congress, May 29–Jun. 2, Toronto, Canada.

Glimcher et al., "Recent studies of the mineral phase in bone and its possible linkage to the organic matrix by protein–bound phosphate bonds", Phil. Trans. R. Soc. Lond., B 304:479–508, 1984.

Glimcher et al., "Recent Studies of Bone Mineral: Is the Amorphous Calcium Phosphate Theory Valid?", J. Crystal Growth, 53: 100–119 (1981).

Graves et al., "Resorbable Ceramic Implants", J. Biomed. Mater. Res. Symposium, No. 2 (Part 1), pp. 91–115 (1971).

Greenfield et al., "Formation chemistry of amorphous calcium phosphates prepared from carbonate containing solutions", Calc. Tiss. Res., 9:152 (1972).

Hirasawa et al., "Manufacture of high purity hydroxyapatite," Chemical Abstracts, 108 (10), p. 166, No. 78193h (Mar. 7, 1988).

Holmes et al., "Surface areas by gas adsorption on amorphous calcium phosphate and crystalliñe hydroxyapatite", Calc. Tiss. Res., 7:163 (1971).

Ishikawa et al., "Effects of preparation in aqueous solution on properties of hydroxyapatites", Dent. Mater. J. 9(1):58 (1990) [CA 113:218168j] (Abstract).

Jones et al., "Poly [L–Lactide] and Poly [L–Lactide] Ceramic Filled Composites: A Long Term in vivo/in vitro Degradation Study," Fifth World Biomaterials Congress, May 29–June 2, 1996, Toronto, Canada.

Kamei et al., "Implantation of hydroxyapatite–bonded polymer," Fifth World Biomaterials Congress, May 29–Jun. 2, 1996, Toronto, Canada.

Kim et al., "Hyaluronan Based Biodegradable Scaffolds for Skeletal Tissue Reconstruction," Fifth World Biomaterials Congress, May 29–Jun. 2, 1996, Toronto, Canada.

Kinoshita et al., "Reconstruction of Mandibular Discontinuity Defects in Dogs using Autogenic Particulate Cancellous Bone and Marrow and Poly(L–lactide) mesh," Fifth World Biomaterials Congress, May 29–Jun. 2, 1996, Toronto, Canada.

Labarthe et al., "Sur la structure et les properié, té, s des apatites carbonaté es de type B phospho–calciques", Ann. Chem., 8:289 (1973).

Ladizesky et al., "Hydrostatic Extrusion of Hydroxyapatite Polyethylene Composite", Fifth World Biomaterials Congress, May 29–Jun. 2, 1996, Toronto, Canada.

Liu et al., "Nano–Apatite/Polymer Composites II. Surface Modification of Nano–Apatite by Grafting of Polyethylene Glycol," Fifth World Biomaterials Congress, May 29–Jun. 2, 1996, Toronto, Canada.

Nylen et al., "Molecular and ultrastructural studies of non–crystalline calcium phosphates", Calc. Tiss. Res., 9:95 (1972).

Oka et al., "Development of Artificial Osteo–Chondral Composite Material," Fifth World Biomaterials Congress, May 29–Jun. 2, 1996, Toronto, Canada.

Otsuka et al., "Effect of particle size of metastable calcium phosphates on mechanical strength of a novel self–setting bioactive calcium phosphate", J. Biomed Mat. Res., 29:25 (1995).

Pool, "Coral chemistry leads to human bone repair", Science, 269:1772 (Mar., 1995).

Posner et al., "Synthetic amorphous calcium phsophate and its relation to bone mineral structure", Bone Mineral Structure, 8:273–281 (1975).

Rey et al., "The carbonate environment in bone mineral: a resolution–enhanced fourier transform infared spectroscopy study", Calcif. Tissue Int., 45:157 (1989).

Rey et al., "Structural studies of the mineral phase of calcifying cartilage", J. Bone Min. Res., 6:515 (1991).

Rey et al., "Preparation of Microporous Ceramic at Low Temperature from Poorly Crystalline Apatite", Symposium Abstract, 1993.

Rizkalla et al., "Effect of Composition on Strength of Bioactive Composites," Fifth World Biomaterials Congress, May 29–Jun. 2, 1996, Toronto, Canada.

Saifullin, R.S., "Physical Chemistry of Inorganic Polymeric and Composite Materials", Chapter 1: Introduction, Ellis Horwood, New York.

Selmani et al., "Bioerodible Polyester Foams for Orthopaedic Tissue Culture," Fifth World Biomaterials Congress, May 29–Jun. 2, 1996, Toronto, Canada.

Termine et al., "Amorphous/Crystalline Interrelationships in Bone Mineral", Calc. Tiss. Res. 1, 8–23 (1967).

Törmälä, P., "Biodegradable Self–Reinforced Composite Materials; Manufacturing Structure and Mechanical Properties", *Clinical Materials* 10:29–34 (1992).

Tung et al., "An intermediate state in hydrolysis of amorphous calcium phosphate", Calcif. Tissue Int., 35:783 (1983).

Blumenthal et al. "Effect of Preparation Conditions on the Properties and Transformation of Amorphous Calcium Phosphate", *Mat Res. Bull* 7(11):1181 (Nov. 1972).

Driessens et al., Calcium Phosphate Bone Cements Encyc. Biomat. and Bioeng., 855–877, 1995.

Fukase, "Setting Reactions and Compressive Strengths of Calcium Phosphate Cements" *J. Dent. Res* 69 (12):1852 (Dec. 1990).

Horioglu et al. "Long Term Follow–Up of Hydroxyapatite Cement (HAC) Implants for Craniofacial Reconstruction" (*21st Annual Meeting of the Society for Biomaterial, San Francisco, CA*, Mar. 18–22, 1995).

Shindo et al. "Facial Skeletal Augmentation Using Hydroxyapatite Cement" *Arch. Otolaryngol Head Neck Surgery* 119:185 (Feb. 1993).

Thissen et al., "Surface modification of bioresorbable polymers by plasma induced graft polymerization", *Fifth World Biomaterials Congress*, May 29–Jun. 2, 1996, Toronto, Canada.

Yasue, et al., "Effect of Adsorption of Succinic Acid on the Formation of Amorphous Calcium Phosphate", *Journal of the Ceramic Society of Japan* (Japanese version), vol. 102, No. 12, pp. 1122–1127. 1994.

BIORESORBABLE CERAMIC COMPOSITES

This application is a continuation-in-part application of co-pending application U.S. Ser. No. 08/650,764 filed May 20, 1996 entitled "Novel Bone Substitution Material and a Method of Its Manufacture" now pending, which is a continuation-in-part application of application U.S. Ser. No. 08/446,182 filed May 19, 1995 entitled "Synthesis of Reactive Amorphous Calcium Phosphates" now issued as U.S. Pat. No. 5,650,176, both of which are herein incorporated in its entirety by reference. This application also is related to several co-pending applications filed on even day herewith, entitled, "Method and Products Related to the Physical Conversion of Reactive Amorphous Calcium Phosphate" U.S. Ser. No. 08/729,344, "Delivery Vehicle" U.S. Ser. No. 08/729,342, "Cell Seeding of Ceramic Compositions" U.S. Ser. No. 08/729,354 and "Orthopedic and Dental Ceramic Implants" U.S. Ser. No. 08/729,343, each of which is incorporated by reference.

FIELD OF THE INVENTION

This invention relates to composite materials containing a poorly-crystalline apatitic calcium phosphate useful as human or animal implantable bioceramics and for other purposes. The invention further relates to moldable, biocompatible composites that can be used for reinforcement in bone fractures, dental implants, bone implants and prostheses and the like.

BACKGROUND OF THE INVENTION

Calcium phosphates are the principal constituent of hard tissues (bone, cartilage, tooth enamel and dentine). Naturally-occurring bone mineral is made of nanometer-sized, poorly-crystalline calcium phosphate with an apatitic structure. The poorly crystalline apatitic calcium phosphate of bone is distinguished from the more crystalline hydroxyapatites and non-stoichiometric hydroxyapatites by its distinctive x-ray diffraction pattern as shown in FIG. 1. Unlike the ideal stoichiometric crystalline hydroxyapatite, $Ca_{10}(PO_4)_6(OH)_2$, with atomic Ca/P ratio of 1.67, the composition of bone mineral is significantly different and may be represented by the following formulae,

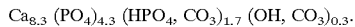

$Ca_{8.3}(PO_4)_{4.3}(HPO_4, CO_3)_{1.7}(OH, CO_3)_{0.3}$.

Bone mineral non-stoichiometry is primarily due to the presence of divalent ions, such as $CO_3^{2-}$ and $HPO_4^{2-}$, which are substituted for the trivalent $PO_4^{3-}$ ions. Substitution by $HPO_4^{2-}$ and $CO_3^{2-}$ ions produces a change of the Ca/P ratio, resulting in Ca/P ratio which may vary between 1.50 to 1.70, depending on the age and bony site. Generally, the Ca/P ratio increases during aging of bone, suggesting that the amount of carbonate species typically increases for older bones. It is the Ca/P ratio in conjunction with nanocrystalline size and the poorly-crystalline nature that yields specific solubility property of the bone minerals. And because bone tissues undergo constant tissue repair regulated by the mineral-resorbing cells (osteoclasts) and mineral-producing cells (osteoblasts), solubility behavior of minerals is important in maintaining a delicate metabolic balance between these cell activities.

Synthetic bone graft material made to closely resemble natural bone minerals can be a useful replacement for natural bone. Acceptable synthetic bone can avoid the problem of availability and harvesting of autologous bone (patient's own bone) and the risks and complications associated with allograft bone (bone from a cadaver), such as risks of viral transmission. An ideal synthetic bone graft should possess a minimum of the following four properties: (1) it should be chemically biocompatible; (2) it should provide some degree of structural integrity in order to keep the graft in place and intact until the patient's own bone heals around it; (3) it should be resorbable so that the patient's own bone ultimately replaces the graft; and, (4) because it may be necessary to incorporate cells and/or biomolecules into the synthetic bone material, it is desirable that the process used to form the material employ low temperatures and chemically mild conditions. Similar criteria are also important for other hard tissue grafts (e.g. cartilage).

These criteria may be met by a material in which parameters, such as Ca/P ratios, crystal size, crystallinity, porosity, density, thermal stability and material purity are controlled. While there have been considerable efforts to synthesize a ceramic material for the use as implants, synthetic hydroxyapatites have most often been used because their chemical formulae are very similar to the naturally occurring mineral in bone. LeGeros R. Z., in *Calcium Phosphates in Oral Biology and Medicine*, Karger Pub. Co., New York, 1991 teaches highly crystalline forms of hydroxyapatite produced by solution precipitation followed by sintering at high temperatures (800–1200° C.). High temperature treatment yields highly stoichiometric hydroxyapatite with crystal sizes on the order of several microns with a Ca/P of 1.67. Such highly crystalline hydroxyapatite is essentially non-resorbable in vivo. It is not replaced by living bone tissue and remains intact in the patient for an undesirably extended period of time.

A number of other approaches to the production of bone substitute material have employed hydroxyapatite produced by a solid-state acid-base reaction of primarily crystalline calcium phosphate reactants. These hydroxy apatite bone substitute materials are sometimes poorly-reacted, inhomogeneous, and have significant crystalline hydroxyapatite content.

Constantz in U.S. Pat. No. 4,880,610 reports on the preparation of calcium phosphate minerals by the reaction of a highly concentrated phosphoric acid with a calcium source in the presence of a base and hydroxyapatite crystals. The resultant product is a polycrystalline material containing a crystalline form of hydroxyapatite minerals. Likewise, U.S. Pat. No. 5,053,212 to Constantz et al. discloses the use of a powdered acid source to improve the workability and mixability of the acid/base mixture; however, a mixed-phase calcium phosphate material similar to that of U.S. Pat. No. 4,880,610 is reported. Recently, Constantz et al. reported in Science (Vol. 267, pp. 1796–9 (Mar. 24, 1995)) the formation of a carbonated apatite from the reaction of monocalcium phosphate monohydrate, alpha-tricalcium phosphate, and calcium carbonate in a sodium phosphate solution, to provide a calcium phosphate material which is still substantially more crystalline in character than naturally occurring bone minerals.

Similarly, Brown et al. in U.S. Reissue No. 33,221 report on the reaction of crystalline tetracalcium phosphate (Ca/P of 2.0) with acidic calcium phosphates. Liu et al. in U.S. Pat. No. 5,149,368 disclose the reaction of crystalline calcium phosphate salts with an acidic citrate.

A number of calcium phosphate bone fillers and cements have been described as "resorbable." Generally, these are compounds comprising or derived from tricalcium phosphate, tetracalcium phosphate or hydroxyapatite. At best these materials may be considered only weakly resorbable. Of these, the tricalcium phosphate compounds have been demonstrated to be the most resorbable and after many years of study they are still not widely used in clinical settings. The tricalcium phosphates are known to have lengthy and somewhat unpredictable resorption profiles, generally requiring in excess of one year for resorption. Furthermore, unless steps are taken to produce extremely porous or channeled samples, the tricalcium phosphates are not replaced by bone. Recently it has been concluded that the "biodegradation of TCP, which is higher than that of Hap [hydroxyapatite] is not sufficient" (Berger et al., Biomaterials, 16:1241 (1995)).

Tetracalcium phosphate and hydroxyapatite derived compounds are also only weakly resorbable. Tetracalcium phosphate fillers generally exhibit partial resorption over long periods of time such as 80% resorption after 30 months (Horioglu et al., Soc. for Biomaterials, Mar. 18–22, pg 198 (1995)). Approximately 30% of microcrystalline HA implanted into the frontal sinus remained after 18 months in cats.

All of these references disclose a chemical reaction resulting in crystalline form of hydroxyapatite solids that has been obtained by reacting crystalline solids of calcium phosphate. There has been little reported on the use of amorphous calcium phosphates (Ca/P of approximately 1.5) as one of the reactants because the amorphous calcium phosphates are the least understood solids among the calcium phosphates and amorphous calcium phosphate has traditionally been considered to be a relatively inert and non-reactive solid.

Amorphous calcium phosphate material has been used as a direct precursor to the formation of a highly crystalline hydroxyapatite compounds under generally high temperature treatments. Such a highly crystalline material is inappropriate for synthetic bone because it is highly insoluble under physiological conditions. Chow et al. in U.S. Pat. No. 5,525,148 report the testing of ACP precursors in a number of reaction schemes but states that slurries of a variety of crystalline calcium phosphates including ACP either alone or in mixtures do not produce a setting cement or act as an effective remineralizing agent.

Brown et al. in U.S. Reissue No. 33,221 report on the formation of crystalline hydroxyapatite for dental cement by reacting an amorphous phase specifically restricted to tetracalcium phosphate (Ca/P of 2.0) with at least one of the more acidic calcium phosphates. Further, Brown et al., does not disclose the preparation or the properties of such a tetracalcium phosphate in amorphous state. Tung in U.S. Pat. No. 5,037,639 discloses the use and application of standard amorphous calcium phosphate paste for the remineralization of teeth. Tung proposes the use of standard inert amorphous calcium phosphate mixed with and delivered through as a chewing gum, mouth rinse or toothpaste, which upon entering oral fluids converts to crystalline fluoride containing hydroxyapatite which is useful to remineralize tooth enamel. Simkiss in PCT/GB93/01519 describes the use of inhibitors, such as Mg ions or pyrophosphate, mixed with amorphous calcium phosphate and implanted into living tissues. Upon leaching of, for example Mg ions, into surrounding bodily fluids, the amorphous calcium-magnesium phosphate converts into a more crystalline form.

There remains a need for a synthetic bone material that more closely mimics the properties of naturally-occurring minerals in bone. In particular, there remains a need to provide synthetic bioceramics which are completely bioresorbable and biocompatible. The use of such a resorbable calcium phosphate in biomedical devices provides many advantages over alternative conventional materials. For instance, it eliminates the need for post-therapy surgery to remove the device and degrades in the human body to biocompatible, bioresorbable products.

Even when the properties of biocompatibility and bioresorbability have been met, the calcium phosphate used in the medical implant may not have the appropriate range of mechanical properties required in a particular application. Biocompatible ceramics have been reported to have excellent compatibility with bone, but the material may lack the necessary strength, flexibility or other mechanical property. Likewise, when used as an adhesive, the material may lack the necessary adhesive strength. Thus, ceramic materials alone, whether superbly biocompatible or not, may not meet all the requirements of an in vivo medical device. Organic polymeric materials have been used as an alternative material because their mechanical properties can be varied as the particular application requires. However, the bone-bonding capability of and/or the bone reossification of organic polymeric materials have not been shown to be as effective as bioactive ceramics.

It is known that composite materials may possess a blend of the attributes and properties of the component materials comprising the composite. Therefore, it is desirable to provide a bioresorbable bone substitute composite material which advantageously possesses superior bioresorbability, biocompatibility and bone reossification capability, while further possessing the high tensile strength, flexibility or other properties otherwise deficient or lacking in the biomaterial alone.

Calcium phosphate composites have been reported, however they lack the complete bioresorbability required of a superior bone substitute material. Calcium phosphates/polymer composites of the prior art generally are prepared with biocompatible polymers. Calcium phosphate fibers or particles are added as a biocompatible, but not bioresorbable, filler to modify the mechanical properties of the polymer matrix. Prior art composites to date have failed to demonstrate a biocompatible composite in which the bioceramic is fully and rapidly resorbable.

SUMMARY OF THE INVENTION

The present invention provides a bioactive ceramic composite material that is biocompatible, bioresorbable and possesses high strength and/or other desirable mechanical properties. The bioactive ceramic composite material may be formed at low temperatures, is readily formable and/or injectable, and yet can harden to high strength upon further reaction. The bioactive ceramic composite material contains a nano-size, poorly crystalline apatitic calcium phosphate solids with Ca/P ratios comparable to naturally occurring bone minerals and having stiffness and fracture toughness similar to natural bone. The bioactive ceramic composite material is strongly bioresorbable and its mechanical properties can be adjusted to meet the demands of the particular therapy and/or implant site. The composite material may be prepared as bone plates, bone screws and other fixtures and medical devices, including veterinarian applications, which are strongly bioresorbable and/or ossifying.

These and other features of the invention are accomplished by the composite material of the invention including a strongly bioresorbable, poorly crystalline apatitic calcium phosphate in intimate contact with a biocompatible supplementary material in an amount effective to impart a selected characteristic to the composite.

The composite material of the invention may be obtained by providing an amorphous calcium phosphate in the presence of a limited quantity of water to produce a hydrated precursor in the form of a putty or paste and promoting the conversion of the amorphous calcium phosphate to a poorly crystalline apatitic calcium phosphate. The conversion is associated with hardening of the paste and produces a poorly crystalline apatitic calcium phosphate. The composite further contains a supplemental material in an amount effective to impart a selected characteristic to the composite.

DEFINITIONS

"Amorphous"—By "amorphous" as that term is used here, it is meant a material with significant amorphous character. Significant amorphous character contemplates greater than 75% amorphous content, preferably greater than 90% amorphous content, and is characterized by a broad, featureless X-ray diffraction pattern. It is recognized that a small degree of crystallinity may exist in the material. However, for the amorphous precursor materials of the present invention, it is preferable that the degree of crystallinity be less than that desired in the product material.

"Bioactive"—"Bioactive" refers to a material that induces hard tissue formation in and about the implant. When implanted in soft tissue, the bioactivity may also require the presence of a growth or trophic factor, or the seeding of the implant with a hard tissue forming cell type.

"Biocompatible"—The term "biocompatible", as used herein, means that the material does not elicit a substantial detrimental response in the host. There is always concern, when a foreign object is introduced into a living body, that the object will induce an immune reaction, such as an inflammatory response that will have negative effects on the host. For example, although hydroxyapatite is generally considered to be "biocompatible", significant inflammation and tissue necrosis have been observed when crystalline hydroxyapatite microcarriers are inserted intramuscularly in animals (see, for example, IJntema et al., *Int. J. Pharm* 112:215 (1994)).

"Bioresorbable"—"Bioresorbable" refers to the ability of a material to be resorbed in vivo. "Full" resorption means that no significant extracellular fragments remain. The resorption process involves elimination of the original implant materials through the action of body fluids, enzymes or cells. Resorbed calcium phosphate may, for example, be redeposited as bone mineral, or by being otherwise reutilized within the body, or excreted. "Strongly bioresorbable", as that term is used herein, means that at least 80% of the total mass of material implanted intramuscularly or subcutaneously is resorbed within one year. In preferred embodiments of the invention, the strongly resorbing poorly crystalline apatitic (PCA) calcium phosphate is characterized in that, when at least 1 g (preferably 1–5 g) of PCA material is implanted at a subcutaneous or intramuscular site, at least 80% of the material is resorbed within one year. In more preferred embodiments, the material will be resorbed within nine months, six months, three months, and ideally one month. Furthermore, particularly preferred materials are characterized in that they can be fully resorbed in the stated time periods. For the purpose of this disclosure, "weakly" resorbable means that less than 80% of the starting material is resorbed after one year.

"Effective Amount"—An effective amount of a supplemental material is an amount sufficient to impart the desired mechanical or chemical property to the composite.

"Hardening"—"Hardening" refers to the process by which the hydrated precursor is transformed into a hardened PCA material. The PCA material is considered to be "hardened" when it is a substantially non-formable solid. Such a hardened PCA material has minimal compressibility and tends to undergo plastic as opposed to elastic deformation.

"Hydrated precursor"—The term "hydrated precursor", as used herein, refers to the paste or putty formed by hydration of the dry PCA precursors in the presence of a limited amount of aqueous solution (i.e., less than approximately 1 mL aqueous solution/1 g precursor powder). The hydrated precursor may comprise both reactants and products, in various combinations, depending on the extent to which the conversion has progressed. Both the "injectable" and "formable" PCA precursor pastes described herein are hydrated precursors. Preferred "injectable" hydrated precursors have a consistency appropriate for delivery through an 18 gauge needle.

"Poorly crystalline apatitic calcium phosphate", "PCA calcium phosphate" and "PCA material", as those terms are used herein, describe a synthetic poorly crystalline apatitic calcium phosphate. The PCA material is not necessarily restricted to a single calcium phosphate phase provided it has the characteristic XRD and FTIR pattern. A PCA calcium phosphate has substantially the same X-ray diffraction spectrum as bone. The spectrum is generally characterized by only two broad peaks in the region of 20–35° with one centered at 26° and the other centered at 32°. It is further characterized by FTIR peaks at 563 $cm^{-1}$, 1034 $cm^{-1}$, 1638 $cm^{-1}$ and 3432 $cm^{-1}$ ($\pm 2$ $cm^{-1}$). Sharp shoulders are observed at 603 $cm^{-1}$ and 875 $cm^{-1}$, with a doublet having maxima at 1422 $cm^{-1}$ and 1457 $cm^{-1}$.

"Promoter"—The term "promoter", as used herein, describes a material or treatment that promotes hardening of a hydrated precursor and may enhance the ACP to PCA calcium phosphate conversion. Some promoters participate in the conversion and are incorporated into the product PCA material; others, known as "passive" promoters, do not participate.

"Reactive"—"Reactive" is used herein to refer to the ability of an amorphous calcium phosphate when mixed with liquid to form a hydrated precursor to undergo conversion to the PCA material of the present invention in the presence of a promoter in association with hardening of the precursor materials. Preferred ACPs are characterized by an ability to convert completely, an ability to convert quickly with hardening, an ability to undergo conversion with otherwise inert compounds and/or an ability to convert into a substantially homogeneous PCA material. Where the ACP is reacted with a second calcium phosphate, the "conversion" can encompass conversion of both the ACP and the second calcium phosphate. The degree of hardening and the kinetics of the hardening process are also important elements of reactivity. Some ACPs are more reactive than others. An ACP is considered "highly reactive" if it undergoes conversion and hardening to a PCA material in the presence of a weak promoter, such as dicalcium phosphate dihydrate ("DCPD") with a grains distribution containing a significant fraction of grain sizes greater than 100 $\mu$m. Preferred highly reactive ACPs produce a hardened PCA material in the presence of weakly promoting DCPD and water at 37° C. in less than twelve hours, with hardening being substantially complete in about one to five hours, and ideally 10–30 minutes.

BRIEF DESCRIPTION OF THE DRAWING

The invention is understood with reference to the following figures, in which:

FIG. 7 presents photomicrographs of tibial defects either untreated (7a) or treated (7a) with a PCA calcium phosphate of the present invention.

DETAILED DESCRIPTION OF THE INVENTION

Figure 1:
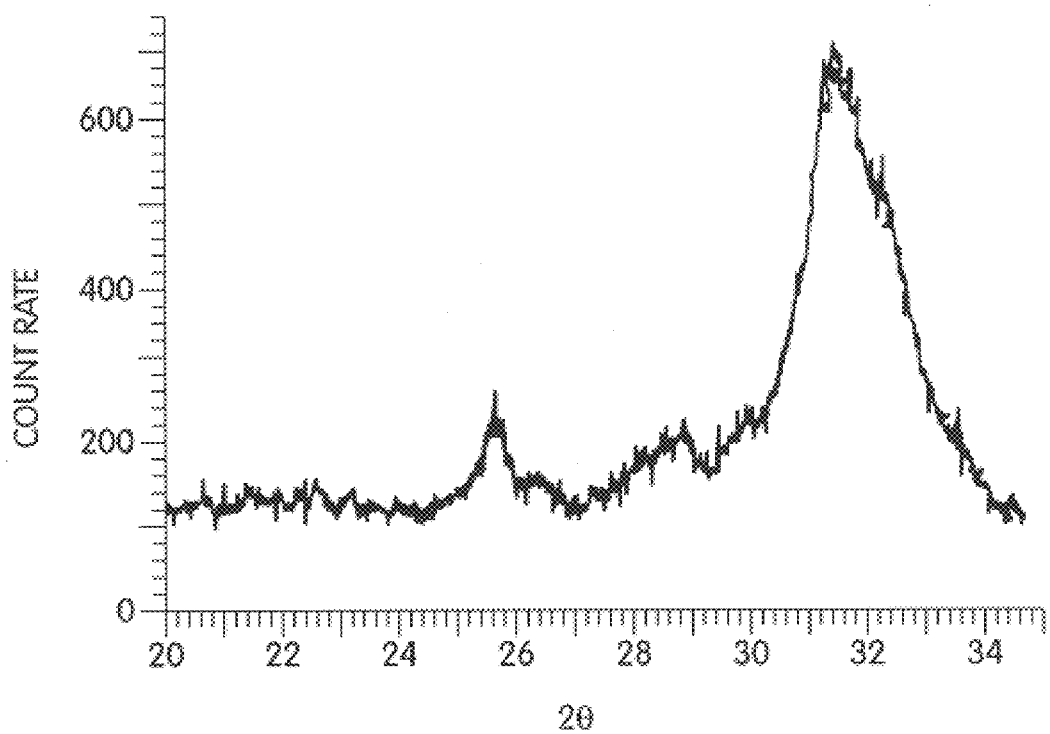
FIG. 1 is an X-ray diffraction pattern of naturally occurring bone.

The present invention is directed to a strongly bioresorbable ceramic composition adapted for use in the repair and growth promotion of bone tissue (a bone substitute composite). The composition comprises a biocompatible and strongly bioresorbable poorly crystalline apatitic (PCA) calcium phosphate combined with a suitable biocompatible matrix or additive.

In one aspect, the invention provides for a strongly bioresorbable composite comprising a bioresorbable, PCA calcium phosphate and additional bioresorbable supplementary materials which can be prepared under mild conditions at room or body temperature (e.g., 20–40° C.). The composite may be applied to bone-contacting surfaces of prosthetic devices, for use as a bone cement. It may be applied directly to bone defects as a filler, where it is capable of promoting the growth of new bone tissue. Alternatively, the composite may be used to fabricate fixtures or devices such as screws and plates, which under appropriate circumstances will be resorbed and replaced by bone. The composite may also be used free standing in non-osseous tissue. When a pharmaceutically active component is added to the composite, it serves as a drug delivery device. Release of the agent may occur over a long period of time after implantation as the composite slowly biodegrades. See, related co-pending application filed even day herewith and entitled "Delivery Vehicle" U.S. Ser. No. 08/729,342, herein incorporated by reference.

The current invention employs a strongly bioresorbable and ossifying PCA calcium phosphate useful as an implantable bioceramic for the treatment of bone disorders and injuries and other biological applications requiring resorbable calcium phosphate. "Full" resorption means that no significant extracellular fragments remain. The resorption process involves elimination of the original implant materials through the action of body fluids, enzymes or cells. Resorbed calcium phosphate may, for example, be redeposited as bone mineral, or by being otherwise reutilized within the body, or excreted. The composites disclosed herein may undergo resorption (i.e., at least 80%) of the total mass (at least 1 g and preferably 1–5 grams) of the implanted PCA material preferably within one year, more preferably within 9 months or 6 months, more preferably in less than 3 months, and most preferable within 1 month.

The PCA calcium phosphate of the invention is characterized by its biological resorbability and substantial absence of crystallinity. Its crystalline character is substantially the same as natural bone, as compared to the higher degree of crystallinity seen in the bone substitute materials known to the art. The inventive PCA calcium phosphate also is biocompatible, that is, no significant detrimental reaction (e.g., inflammation or fibrosis) is induced in the host by the implanted composite material. Materials which induce a medically acceptable level of inflammation or fibrosis are considered biocompatible. In addition, the material is also bioactive, in that apposition of new bone at the host/composite interface occurs.

In an important aspect of the invention, the ease of use of the inventive implantable bioceramic material in a surgical or manufacturing setting is significantly improved over other bone substitute composite materials known in the art. Specifically, the reaction which forms PCA calcium phosphate may be initiated outside the body and proceeds slowly at room temperature thereby minimizing any possibility that the material will "set up" prior to heating (e.g. prior to application to the surgical site or in the manufacturing incubation). The reaction accelerates significantly at about 37° C. causing the reaction to harden. The hardened PCA calcium phosphate alone has a durometer and bulk modulus similar to traditional blackboard chalk. In some instances, hardened PCA material will be associated with the presence of unreacted precursors, promoters, and/or supplemental materials, side products and by-products.

By formulating the PCA material as a composite, mechanical properties of the material may be improved. In some formulations, the hardened PCA calcium phosphate alone is brittle and has a durometer and bulk modulus similar to traditional blackboard chalk. The preparation of PCA calcium phosphate as a composite material is desirable in order to alter the mechanical properties for some medical uses. Furthermore, the consistency, formability and hardness of the PCA calcium phosphate, as well as the reaction speed, may be varied according to the therapeutic need by selection of the appropriate supplementary materials from which to prepare the implantable bioceramic composite material of the invention.

Preparation of the implantable bioceramic composite. The composite material of the present invention is prepared by combining the PCA calcium phosphate of the invention with a selected supplementary material. The PCA calcium phosphate may serve as the reinforcing material, the matrix or both. The PCA calcium phosphate of the invention in it's initial paste form (i.e., as a hydrated precursor) typically maintains a pH of about 6–7 and is therefore compatible with a wide range of additives without deleterious effect. The supplementary material is selected based upon its compatibility with calcium phosphate and its ability to impart properties (biological, chemical or mechanical) to the composite, which are desirable for a particular therapeutic purpose. For example, the supplementary material may be selected to improve tensile strength and hardness, increase fracture toughness, alter elasticity, provide imaging capability, and/or alter flow properties and setting times of the PCA calcium phosphate.

The supplementary material may be added to the PCA calcium phosphate in varying amounts and in a variety of physical forms, dependent upon the anticipated therapeutic use. By way of example only, the supplementary material may be in the form of sponges (porous structure), meshes, films, fibers, gels, filaments or particles, including micro- and nanoparticles. The supplementary material itself may be a composite. The supplementary material may be used as a particulate or liquid additive or doping agent which is intimately mixed with the resorbable PCA calcium phosphate. The supplementary material may serve as a matrix for the PCA calcium phosphate, which is embedded or dispersed within the matrix. Alternatively, the PCA calcium phosphate may serve as a matrix for the supplementary material, which is dispersed therein. The supplementary material may be applied as a coating onto a PCA calcium phosphate body, for example, as a post-fabrication coating to retard resorption time or otherwise affect the bioceramic material properties. Lastly, the supplementary material may be coated with PCA calcium phosphate.

The supplementary materials are desirably biocompatible, that is, there is no detrimental reaction induced by the material when introduced into the host. In many instances, it is desirable that the supplementary material also be bioresorbable. In many preferred embodiments, the supplementary material will have an affinity for calcium, phosphate or calcium phosphates which will enhance the strength of the PCA calcium phosphate/supplementary material interface. The affinity may be specific or mediated through non-specific ionic interactions. By way of example only, suitable bioerodible polymers for use as a matrix in the composite include, but are not limited to, collagen, glycogen, chitin, celluloses, starch, keratins, silk, nucleic acids, demineralized bone matrix, derivativized hyaluronic acid, polyanhydrides, polyorthoesters, polyglycolic acid, polylactic acid, and copolymers thereof. In particular, polyesters of α-hydroxycarboxylic acids, such as poly(L-lactide) (PLLA), poly(D,L-lactide) (PDLLA), polyglycolide (PGA), poly(lactide-co-glycolide) (PLGA), poly(D,L-lactide-co-trimethylene carbonate), and polyhydroxybutyrate (PHB), and polyanhydrides, such as poly(anhydride-co-imide) and co-polymers thereof are known to bioerode and are suitable for use in the present invention. In addition, bioactive glass compositions, such as compositions including $SiO_2$, $Na_2O$, $CaO$, $P_2O_5$, $Al_2O_3$ and/or $CaF_2$, may be used in combination with the PCA calcium phosphate of the invention. Other useful bioerodible polymers may include polysaccharides, peptides and fatty acids.

Bioerodible polymers are advantageously used in the preparation of bioresorbable hardware, such as but not limited to intermedulary nails, pins, screws, plates and anchors for implantation at a bone site. In preferred bioresorbable hardware embodiments, the supplementary material itself is bioresorbable and is added to the PCA calcium phosphate in particulate or fiber form at volume fractions of 1–50% and preferably, 1–20 wt %. In some preferred embodiments, the bioresorbable fiber is in the form of whiskers which interact with calcium phosphates according to the principles of composite design and fabrication known in the art. Such hardware may be formed by pressing a powder particulate mixture of the PCA calcium phosphate and polymer. In one embodiment, a PCA calcium phosphate matrix is reinforced with PLLA fibers, using PLLA fibers similar to those described by Törmälä et al., which is incorporated herein by reference, for the fabrication of biodegradable self-reinforcing composites (*Clin. Mater.* 10:29–34 (1992)).

The implantable bioceramic composite may be prepared as a paste by addition of a fluid, such as water or a physiological fluid, to a mixture of a PCA calcium phosphate and a supplemental material. Alternatively, a mixture of the supplementary material with hydrated precursor powders to the PCA calcium phosphate can be prepared as a paste or putty. In cases where the supplementary material is to be dispersed within or reacted with a PCA calcium phosphate matrix, water may be added to one of the precursor calcium phosphates to form a hydrated precursor paste, the resulting paste is mixed with the supplementary material, and the second calcium phosphate source is then added. Alternatively, the calcium phosphate sources which make up the PCA calcium phosphate precursor powder may be premixed, water may then be added and then the supplementary material is added. In those cases where it is desirable to have the supplementary material serve as the matrix, the fully hardened PCA calcium phosphate will be prepared in the desired form which will most often be of controlled particle size, and added directly to the matrix forming reaction (e.g., to gelling collagen). These materials may then be introduced into molds or be otherwise formed into the desired shapes and hardened at temperatures ranging from about 35–100° C. A particularly useful approach is to form the composite precursor paste into the approximate shape or size and then harden the material in a moist environment at 37° C. The hardened composite may then be precisely milled or machined to the desired shape for use in the surgical setting. The amount of particular PCA calcium phosphate to be incorporated into the supplemental material matrix will most often be determined empirically by testing the physical properties of the hardened composite according to the standards known to the art.

In preferred embodiments, the reactants are mixed outside of the body, yielding a formable composite material comprising a hydrated precursor material having a physical integrity suitable for application to a surgical site. Conversion to the PCA material generally is complete after application to the surgical site. The supplemental materials will generally be in final form when added to the PCA calcium phosphate or hydrated precursor paste, although the use of polymer monomers and precursors, added to the paste is considered within the scope of the invention. In a preferred embodiment, the conversion reaction is initiated by adding distilled water to a mixture of the dry precursor components to form a thick hydrated precursor in the form of a paste or putty. Other aqueous agents such as buffers, saline, serum or tissue culture medium may be used in place of distilled water. In other preferred embodiments, sufficient water may be added to the precursor powders to form a paste which is readily injectable with an 18 gauge needle. Bioceramic composite materials of the invention generally harden in less than five hours and substantially harden in about one to five hours under physiological conditions, and preferably in about 10–30 minutes. Most often the resulting bioresorbable PCA calcium phosphate will be calcium deficient with a calcium to phosphate ratio of less than 1.5 as compared to the ideal stoichiometric value of approximately 1.67 for hydroxyapatite.

The invention also provides a test for identifying suitable reactive PCA calcium phosphate and reactive precursors for use in the composites of the invention. Specifically, precursors are combined, are hydrated with a limited amount of water (so that a paste or putty is formed), and are allowed to harden into a PCA material. Desirable precursors are capable of hardening in a moist environment, at or around body temperature in less than 5 hours and preferably within 10–30 minutes. Components which harden in this way may then be placed intramuscularly or subcutaneously in a test animal and checked for biological resorbability. Desirable materials are those that, when implanted as a 1–5 g pellet, are at least 80% resorbed within one year. Generally, it is easier to test resorption of gram quantities of material in subcutaneous sites.

Medical devices prepared from the inventive composites using all bioresorbable supplementary materials will themselves be resorbable and in preferred embodiments, strongly bioresorbable. The composites used in these devices may be designed to impart the desired mechanical properties to the devices making them useful in the surgical setting (e.g., orthopedic pins and screws). Following placement in the host, the devices will gradually be replaced by bone i.e., ossification of the bone site occurs. This is in contrast to merely biocompatible materials where the device promotes apposition of bone at its surface, but does not resorb so as to ossify the implant site. While resorption time in vivo will generally depend upon the actual identity of the supplementary material, as well as the graft size and location, for those composites with less than 20% vol/vol supplementary material, resorption of the PCA calcium phosphate and ossification at the implant site will be generally complete in less than six months and most often in about one month. In some cases, the resorbable supplemental material will still be present embedded in the newly formed bone, thus being resorbed over a longer time course than the PCA calcium phosphate. The use of resorbable hardware obviates the need for a subsequent surgical procedure to remove the device.

The resorbability of the implantable bioceramic composite material of the instant invention is attributable in part to the porosity, crystallinity and chemical composition of its component materials. The bioceramic composite material of the invention comprises a poorly crystalline apatitic calcium phosphate, substantially similar to that found in natural bone. Lack of crystallinity in apatites is associated with somewhat increased solubility in aqueous systems compared to other more crystalline species, and thus the low crystallinity and/or presence of stable amorphous apatitic domains is believed to promote its resorbability in biological systems. Porosity facilitates both the penetration of cells and cell processes into the bone substitute material matrix and the diffusion of substances to and from the matrix interior. Accordingly, low porosity composite materials resorb more slowly in vivo than those of high porosity.

In preferred embodiments, in order to optimize ossification, the devices and objects may be seeded with bone forming cells. This is most easily accomplished by placing the device in contact with a source of the patient's own bone forming cells. Such cells may be found in bone-associated tissue, blood or fluids, including exogenous fluids which have been in contact with bone or bone materials or regions, including the periosteum, cancellous bone or marrow. In the case of devices such as screws and pins, the introduction of which into bone is accompanied by breach of the periosteum and/or bleeding, no further seeding is required. For plates, which oppose only cortical bone, induction of a periosteal lesion which will contact the device is recommended. In yet other embodiments, it will be useful to surgically prepare a seating within the bone by removing a portion of cortical bone at the implant site. Other steps may also be taken to augment ossification, including introduction of bone forming cells harvested from the patient into the graft, or incorporation of trophic factors or bone growth inducing proteins into, or onto the device. Use of non-autologous bone cells is also within the scope of the invention if the desired amount of bone regeneration occurs prior to host rejection of the bone forming cells. Thus, cells or tissues obtained from primary sources, cell lines or cell banks may all be useful in certain embodiments. See, United States application filed on even day herewith entitled, "Cell Seeding in Ceramic Compositions" U.S. Ser. No. 08/729, 354 and incorporated herein by reference.

Bioresorbable polymers may also be used in the preparation of bone glues or putties for use in load bearing situations. Supplementary materials may be added to the composite to increase compressibility and load-bearing properties of the bone glue. In particular, carbon fibers or other reinforcing fibers may be added to the composite. In the production of fiber-reinforced bone substitute glues, it may be advantageous to plasma etch the fibers to improve the quality and strength of the calcium phosphate/fiber interface. PCA calcium phosphate may also be hardened at 37° C., pulverized or otherwise fragmented, and mixed with known binders such as bone glues cements, fillers, plasters, epoxies, other calcium phosphates, or gels such as, but not limited to, calcium sulfate, tricalcium phosphate, tetracalcium phosphate, alginate, collagen, or commercially available products such as Endobone (Merck), Hapset (Lifecore Biomedical), SRS (Norian), Bonesource (Leibinger), Colograft (Zimmer), Osteograf (CereMed), and Simplex (Howmedica). For applications where hardened PCA calcium phosphate will be dispersed within the binder substance, most often the binder will be prepared by methods known to the art and mixed with the particulate PCA calcium phosphate in approximately equal volumes, although actual proportions will be varied in ways known to the art to produce compositions of desired consistency, workability and adherence.

In yet another embodiment, braided sutures, typically prepared from polyester, maybe coated with the PCA calcium phosphate of the invention, to improve their biocompatibility. Coated sutures may be prepared by dipping the suture into a slurry containing finely divided particulate PCA calcium phosphate. The affinity of the suture for the PCA calcium phosphate coating may be improved by surface treating either the suture, the PCA calcium phosphate particle or both. Surface treatments include plasma etching and/or chemical grafting.

In other embodiments, a composite is provided comprising PCA calcium phosphate and a non-resorbable or poorly resorbable material. Suitable non-erodible or poorly erodible materials include dextrans, polyethylene, polymethylmethacrylate (PMMA), carbon fibers, polyvinyl alcohol (PVA), poly(ethylene terephthalate)polyamide, bioglasses, and those compounds listed previously for use in bone glues or putties. In one embodiment, carbon fibers may be used to reinforce the PCA calcium phosphate. In such applications, fibers lengths of 0.05 μm–20 cm and fiber content typically in the range of 0.01–50 vol % are used depending upon the intended use.

Another use is to permanently imbed useful objects, such as a pin or reinforcing mesh, into bone itself. The object serves as an anchor for the stable attachment to natural bone. This is particularly useful in the attachment of ligaments and tendons to bone. Objects comprising bioresorbable and ossifying PCA calcium phosphate and a suitable non-resorbable hardware may be placed into a bone and further secured with additional PCA calcium phosphate material or composite material in a bone glue formulation. The hardware then becomes embedded into the bone following reossification of the PCA calcium phosphate.

Calcium phosphates, including hydroxyapatites, tricalcium phosphate and tetracalcium phosphate, may be used as the non-resorbable supplementary materials of the inventive composites, in particular to maintain biocompatibility of the composite. In these embodiments, the calcium phosphates are most likely to be non-resorbable and to be pre-hardened in a particulate, fiber-like or other preformed shape. These solid calcium phosphate additives may further be compressed, sintered or otherwise modified prior to mixture with the PCA calcium phosphate.

In yet another embodiment of the invention, a composition is prepared by intimately mixing the PCA calcium phosphate with an additive which alters the resorption properties, setting time and/or flow characteristics of the composite. For example, silicone oil or other lubricating polymers or liquids may be added to the composite to improve the flow characteristics of the composite for delivery to the host by syringe. The lubricant is preferably biocompatible and capable of rapid leaching from the bone substitute material composite following solidification of the PCA calcium phosphate in vivo. Suitable lubricants include, by way of example only, polymer waxes, lipids and fatty acids. Lubricants may be used in a concentration of about 0.1 to about 30 wt %.

In yet another embodiment of the invention, the composite contains a PCA calcium phosphate and a radiographic supplemental material for imaging the implant in vivo. Suitable electron dense materials include materials known in the art, such as titanium and barium oxide, in clinically relevant concentrations.

In a preferred embodiment, a bioceramic material may be prepared with a Young's Modulus similar to bone by preparing a polyethylene composite containing the resorbable PCA calcium phosphate of the invention. In other preferred embodiments, a resorbable polymer such as poly(L-lactide) or collagen may be used to prepare a composite with similar properties as normal bone. In another preferred embodiment, the particulate PCA calcium phosphate is pressed into a desired shaped and the pressed body is impregnated with the supplementary material. In yet another preferred embodiment, hydrated precursor materials of the PCA calcium phosphate are mixed with the supplementary material and the conversion to the bioceramic material is initiated in the presence of the supplementary material. Generally, the inventive PCA calcium phosphate will be present in the composite at a volume fraction of less than 0.7 and preferably less than 0.5.

The composition of the invention may be prepared in any conventional manner useful in the preparation of composite materials, including but not limited to blending, mixing, alloying, laminating, filament winding and pultruding. A variety of strategies for the design and fabrication of polymer/inorganic composites, fibers and matrix resins and other reinforcement technologies are useful and will be known in the art. Guidance regarding the preparation of HA/polyethylene composites can be found in Bonfield in *Introduction of Bioceramics* at pp. 299–303 and the references therein, all incorporated by reference. Additional guidance may be obtained from the following sources, incorporated herein by reference: Jang, *Advanced Polymer Composites: Principles and Applications*, ASTM Int'l, Materials Park, Ohio (1994); Opila et al. Eds., *Polymer/Inorganic Interfaces*, Materials Research Soc., Pittsburgh, Pa. (1993); Saifullin, *Physical Chemistry on Inorganic, Polymeric and Composite Materials*, Ellis Horwood, N.Y. (1992); Ducheyne et al. in *Introduction to Bioceramics*, Hench and Wilson, Eds. World Scientific Publishing, N.J. pp 281–298 (1993); and Törmälä, *Clin. Materials* 10:29–34 (1992).

The bioceramic composite material may also be prepared with varying degrees of porosity. In one embodiment, the use of a dry mixture of controlled particle size reactants leads to a porous composite material. Other methods of promoting porosity, such as chemical or physical etching and leaching, may be employed.

In yet another embodiment, a mixture of the PCA calcium phosphate and a polymeric supplemental material may be extruded by conventional polymer extrusion techniques to form tubes, fibers and other shapes. For extrusion purposes, the supplemental material is preferably an organic polymer. In some situations, where increased tensile strength and modulus and stiffness are desired, the composite may be extruded or otherwise mechanically deformed to align polymer chains to increase composite strength. The composite may also be hardened under pressure and/or heat to provide a composite that is more dense, tougher and resorbs at a slower rate in vivo. In general, conditions which cause rapid conversion of the PCA calcium phosphate to the more crystalline HA should be avoided.

In some embodiments, it may be desirable to modify the surface of the PCA calcium phosphate and/or the supplemental material in order to improve the interface between the two materials and/or to improve the affinity of pharmaceutically active agents, e.g., proteins, to the composite. For example, the inventive calcium phosphate may be grafted with moieties which show affinity for proteins and other organic molecules. Alternatively, the composite may be subjected to surface treatments, such as plasma etching to improve interfaces between the two phases as is known in the art.

For some embodiments in which the composite material is prepared and hardened in advance of its surgical use, and where storage is desired, it may be desirable to enhance the stability of the poorly crystalline state of the composite. In such cases, exposure of the preformed composite to crystallization inhibitors may be useful. Inhibitors may be added to the aqueous medium used to prepare the inventive PCA calcium phosphate, or the finished composite or objects made from it may be exposed to inhibitory substance subsequent to fabrication. Suitable such inhibitors include, but are not limited to, magnesium ion, carbonate ion, poly (L-glutamate), polyacrylate, phosvitin, casein, and protein-polysaccharides. Guidance for the use of such compounds can be found in LeGeros in *Monographs in Oral Science* Vol. 15 pp 84–107; LeGeros *Prog. Crystal Growth Charact.* 4:1–45 (19810; and Termine et al. *Arch. Biochem. Biophys.* 140:318–325 (1970), incorporated herein by reference.

The inventive composite may also be used as a drug delivery system by incorporation of a biologically active material into the composite. Further details are found in co-pending application filed on even day herewith and entitled "Drug Delivery Vehicle", U.S. Ser. No. 08/729,342, which is herein incorporated by reference.

Preparation of reactive amorphous precursor to PCA calcium phosphate. A reactive amorphous calcium phosphate (ACP) is desirably used to form a poorly- or nanocrystalline synthetic apatitic calcium phosphate that provides bioactivity, bioresorbability and structural integrity in the above-described composites. This novel amorphous material can be converted at or below 37_° C. to form a bone-like material consisting of PCA calcium phosphate. This amorphous calcium phosphate is highly reactive towards other calcium phosphates and is capable of reacting at room temperature with a variety of calcium- or phosphorus-bearing compounds which are not conventionally considered to be reactive to ACP, for example CaO, $CaCO_3$ and calcium acetate. By "amorphous" as that term is used herein it is meant a material with significant amorphous character. Significant amorphous character contemplates greater than about 75% amorphous content and preferably greater than about 90% amorphous content and is characterized by a broad, featureless X-ray diffraction pattern. It is recognized that a small amount of crystallinity may exist in the material, however, it is anticipated that the crystallinity will not be greater than the degree of crystallinity desired in the product PCA calcium phosphate.

Figure 2:
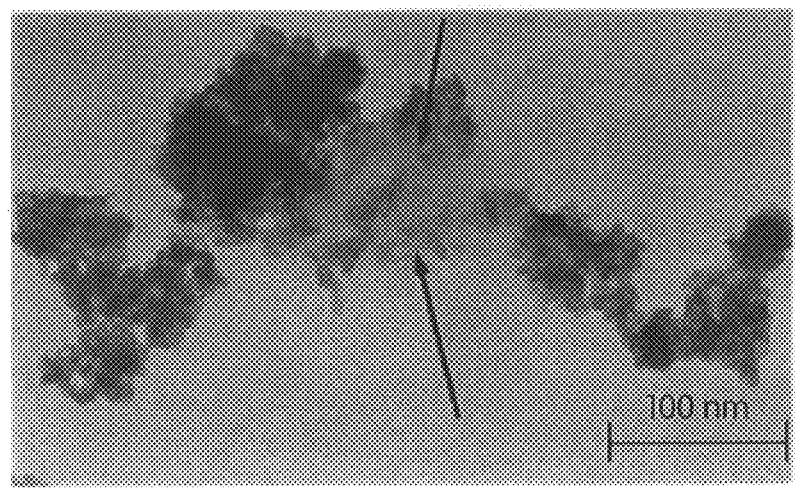
FIG. 2 is a high-resolution transmission electron micrograph of the reactive amorphous calcium phosphate illustrating the nanometer-sized grains in clusters with relatively unclear boundaries and partially immersed in shapeless form (arrows)

ACP particles of less than 1000 Å, preferably 200–500 Å, and most preferably 300 Å, are initially formed, the further growth of which are curtailed by rapid precipitation of the product from solution. In FIG. 2, a high-resolution transmission electron micrograph of the ACP precipitate is shown to illustrate the morphological characteristics and the angstrom-scale nature of the preferred reactive amorphous calcium phosphate. Note the unclear boundaries separating the globule-like clusters, lacking clear edges and surfaces, in contrast to crystalline material.

During reaction of calcium and phosphate ion sources to form an ACP, a third ion may be introduced in the solution so that these ions are incorporated in the amorphous precipitate structure instead of trivalent $PO_4^{3-}$ group(s). Because some $PO_4^{3-}$ is replaced by the third ion, the overall $PO_4^{3-}$ decreases, thus increasing the Ca/P ratio of the amorphous precipitate (as compared to standard amorphous calcium phosphate) and modifying the valence or charge state of the calcium phosphate. The amorphous solids then may be rapidly freeze-dried to preserve the chemical and physical properties of the material. The amorphous solids then may be treated under specific conditions selected to promote removal of at least some of the third ion. In the case of carbonate, specific temperature and pressure conditions lead to the reduction of total carbon, presumably as gaseous carbon dioxide from the amorphous solid, while maintaining the amorphicity.

In a preferred embodiment, where carbonate is present in the ACP, the ACP powder is heated to drive off remaining free water, water of hydration and to remove carbon, presumably through the decomposition of $CO_3^{2-}$ into $CO_2$ and oxygen. The heating step is carried out at a temperature less than 500°–600° C. but more than 400_° C., so as to prevent conversion of the amorphous calcium phosphate into crystalline hydroxyapatite. Heating is carried out at a temperature in the range of about 300–500° C., and preferably 450–460° C., for about one to six hours. Heating for extended periods, e.g., greater than about 24 hours, has been found to degrade the ACP reactivity.

The resultant material is an amorphous solid with a higher Ca/P ratio than is typically found in amorphous calcium phosphates, which is generally reported to be 1.50. Further, removing carbon from the material is believed to result in vacancies in the interstitial structure within the amorphous solids, rendering it a highly reactive solid. There may be several possible vacancy sources. The material possesses a porosity which promotes reactivity by various means, such as increased surface area. The material may also undergo a change in the stoichiometry balance upon removal of the third ion. This stoichiometry change may result in a charge imbalance which is responsible for the increased reactivity of the amorphous calcium phosphate.

It is desirable to maintain the amorphous property of the material throughout the entire process. If crystallinity in its entirety (single crystalline regions) or even in local domains (microcrystalline regions) is introduced during the process or in the final product, the solid has been found to lose its reactivity. The resultant highly reactive calcium phosphate is amorphous in nature and has a calcium to phosphorous ratio in the range of 1.55 to 1.65. In a preferred embodiment, the amorphous calcium phosphate has a Ca/P ratio of about 1.58.

Additional information on reactive amorphous calcium phosphates may be found in co-pending U.S. Ser. No. 08/446,182 filed on May 19, 1995 and entitled "Synthesis of Reactive Amorphous Calcium Phosphates", now issued as U.S. Pat. No. 5,650,176, and in co-pending application U.S. Ser. No. 08/650,764, filed on May 20, 1996 and entitled "Novel Bone Substitute Material and a Method of Its Manufacture", which are herein incorporated in its entirety by reference.

Preparation of PCA calcium phosphate. The reaction to obtain PCA calcium phosphate employs at least one amorphous calcium phosphate (ACP) precursor, and preferably employs an activated or reactive ACP. In some instances, the reaction may employ only one precursor ACP which is converted in a controlled fashion in part or whole to the PCA calcium phosphate of the invention through the action of a promoter. Alternatively, the reaction may employ one or more additional precursors (preferably a calcium and/or a phosphate source), which react with the ACP to yield the PCA calcium phosphate of the invention. Reactions which can be initiated outside of the body, carried out in a paste-like configuration and which can be significantly accelerated at 37° C. leading to a hardened calcium phosphate product are greatly preferred. Reactions may be carried out at ambient or body temperatures.

The conversion of ACP to PCA calcium phosphate is initiated by addition of a limited amount of water to an ACP powder sufficient to prepare a paste or putty. Fluid addition is typically limited to about 1 ml fluid/1 g powder. As the conversion proceeds it is accompanied by hardening of the paste. The conversion of ACP to PCA calcium phosphate proceeds in a controlled fashion as a paste or putty which hardens predictably and which has utility in dental, orthopedic, drug delivery, cell therapy or other therapeutic applications.

The conversion (and concomitant hardening) of the reactive ACP into a PCA calcium phosphate is promoted by addition of one or more "promoters" to the ACP powder. Promoters may be "passive", in that they do not participate in the reaction. Suitable passive promoters include, but are not limited to, materials or treatments that have previously been described as promoting conversion of a calcium phosphate material into HA. For example, water and heat, nucleation causing substances and/or catalysts may be used as promoters. Although not bound to any particular mode of operation, it is presumed that a catalyst or nucleation causing substance provides surface area having reactive surfaces which promote conversion of ACP into the PCA material. Additional suitable passive promoters include $Al_2O_3$, mica, glass and sand. Passive promoters are desirably insoluble or poorly soluble in water, are in granular form with a particle size in the range of 1–200 micrometers, and, optionally, are bioresorbable.

When amorphous calcium phosphate is used as the sole precursor to produce a resorbable bioceramic material, it is important to control the natural tendency of the ACP to convert to highly crystalline hydroxyapatite. On the other hand, the time course of conversion should be fast enough to have surgical utility. One approach is to combine a precursor ACP containing an inhibitor of crystal formation with an ACP that does not contain an inhibitor of crystal formation (e.g., a promoter). The reactants may be mixed in a dry state, with the appropriate particulate size and an excess of the inhibitor-containing ACP. The reactants can then be hydrated by addition of water, followed by an elevation in temperature, such as that which occurs following introduction into the body, to convert the reactants to the PCA calcium phosphate of the invention. Particularly suitable in this regard are substances which provide reactive surfaces which weakly promote apatitic crystallization to produce a poorly crystalline apatitic calcium phosphate.

The promoter may also be a "participatory" promoter, in that the promoter itself is converted to the PCA material. A particularly preferred participatory promoter is a second calcium phosphate. The reaction preferably occurs at patient body temperature upon mixing of the ACP powder with calcium phosphates in the presence of a fluid, such as but not limited to, water, saline, buffer solution, serum or tissue culture medium. Depending upon the amount of fluid added the mixture of amorphous calcium phosphate of the present invention and acidic calcium phosphate results in a highly formable and/or highly injectable paste (i.e., hydrated precursor) with varying degrees of consistency depending upon the exact formulation used. The ACP precursor may be reacted with a second calcium source (including a second ACP) using any reaction promoting technique. Such reactions include acid/base, displacement, substitution, and hydrolysis reactions as well as purely physical and mechanical reactions.

Under any reaction scheme it is important that the ACP retains significant amorphous character throughout the reaction. Specifically, the overall crystallinity within the starting ACP does not exceed that desired in the end product. Thus certain reaction schemes may require stabilization of the amorphous nature of the ACP throughout the reaction period. Examples of suitable crystallization inhibitors known to the art include carbonate, magnesium and pyrophosphates. Additional guidance for the use of inhibitors of crystallization may be found in LeGeros, Ibid. and Elliot, *Structure and Chemistry of the Apatites and Other Calcium Orthophosphates*, Elsevier, Netherlands, 1994, herein incorporated by reference. Other methods of activation known to the art, such catalysis or the use of ionic solvents or promoters of nucleation, may also be used to promote reaction between substituents. In many forms of the current invention, at least one of the precursors must be activated so as to react with the other components at physiological conditions as described hereinabove.

Appropriate calcium phosphates include both basic and acidic calcium phosphates which provide the appropriate stoichiometry for reaction to obtain a PCA calcium phosphate. Suitable calcium phosphates include, but are in no way limited to, calcium metaphosphate, dicalcium phosphate dihydrate, heptacalcium decaphosphate, tricalcium phosphates, calcium pyrophosphate dihydrate, crystalline HA, PCA calcium phosphate, calcium pyrophosphate, monetite, octacalcium phosphate and ACP. In one embodiment, an acidic (pH 5–7) calcium phosphate is used. In another embodiment, the inventive PCA calcium phosphate is used in particulate form as the second component. In yet another embodiment, fine particulate crystalline HA is used as the second component. Other solids which provide a source of phosphate or calcium, such as by way of example only, CaO, $CaCO_3$, calcium acetate, and $H_3PO_4$, may be mixed to form a final product to yield a desired Ca/P ratio close to natural bone. The second calcium phosphate reactant may be of any crystalline structure and should be chosen so as to be reactive with the first ACP either directly or through the use of a reaction promoting vehicles, such as ionic solvents or catalysts. Preferred second calcium phosphate reactants are those which tend themselves to undergo conversion to HA through an intermediate PCA calcium phosphate phase. It may be desirable to provide the second component in the amorphous or poorly crystalline state, as well. Suitable reactants and appropriate reaction conditions may be determined by mixing reactants and water, and demonstrating rapid hardening at about 37° C.

Figure 3A:
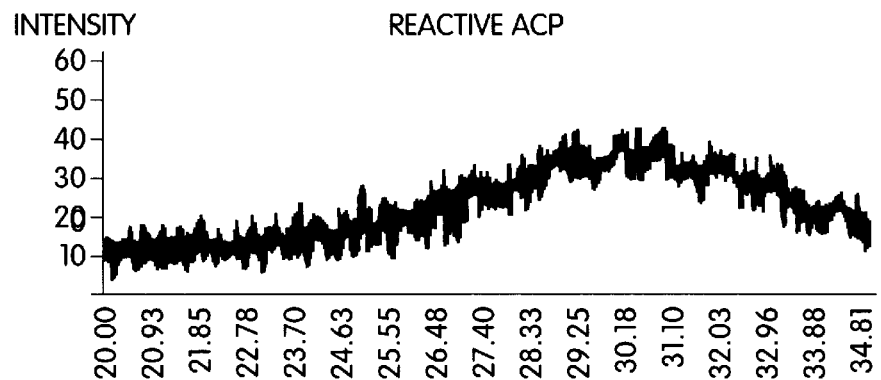
FIG. 3 shows X-ray diffraction patterns of (a) a reactive amorphous calcium phosphate; and (b) a dicalcium diphosphate and (c) the product poorly crystalline apatitic calcium phosphate.
Figure 3B:
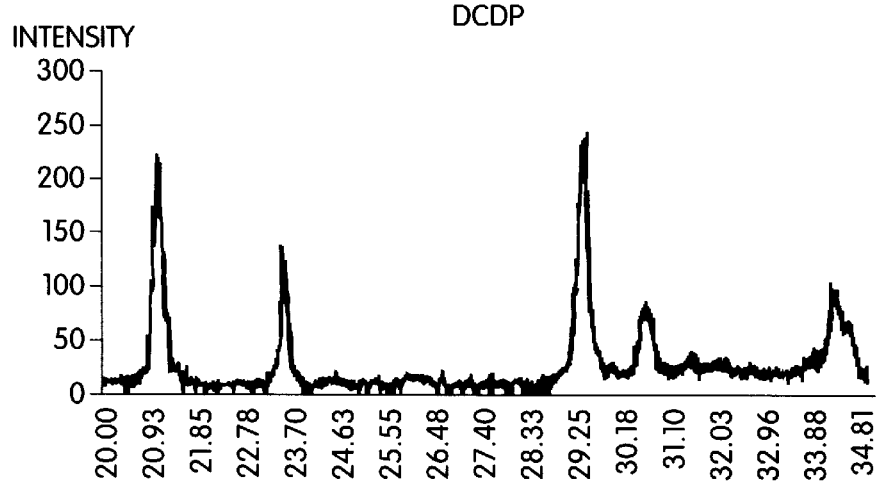
Figure 3C:
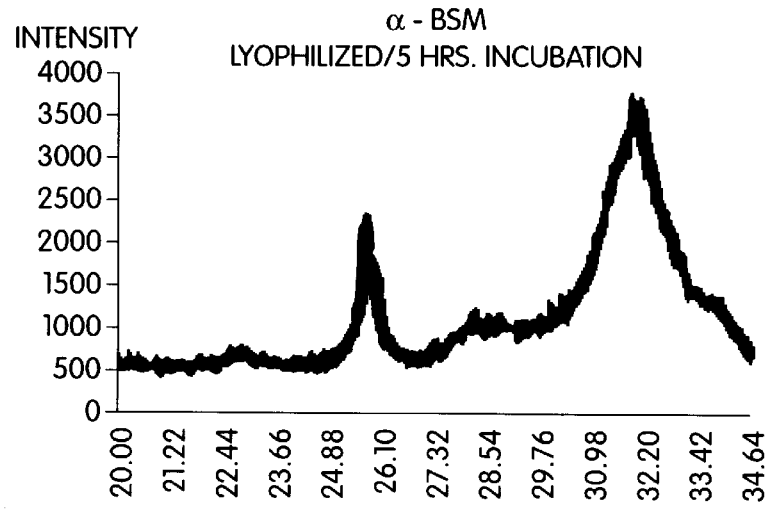

The second calcium phosphate is often crystalline, as is evidenced by the presence of sharp diffraction peaks of a typical calcium phosphate reactant, DCPD, as shown in the X-ray diffraction pattern (FIG. 3(*h*)). In contrast, the reactive ACP is amorphous and shows no identifiable peaks by X-ray diffraction (FIG. 3(*a*)). Despite its higher crystallinity, however, in a preferred embodiment DCPD is consumed in the reaction with reactive ACP and the product PCA calcium phosphate is of much reduced crystallinity (FIG. 3(*c*)), as compared to DCPD.

Because at least one of the reactants is amorphous and highly reactive, the reaction proceeds at room temperature or body temperature to provide an apatitic material having a poorly-crystalline or microcrystalline microstructure. The reaction also is substantially complete, thereby insuring that all calcium and phosphate of the mixture are consumed by the resultant apatitic product. This permits reliable manufacture of PCA calcium phosphate simply by selection of the relative proportions of the starting amorphous and secondary calcium phosphates. It is desirable to maintain a calcium to phosphate ratio of about 1.2–1.68, preferably less than 1.5, and most preferably about 1.38.

Further information on the preparation of PCA calcium phosphate can be found in co-pending U.S. Ser. No. 08/446, 182 now issued as U.S. Pat. No. 5,650,176, and Ser. No. 08/650,764, which are herein incorporated by reference.

The invention is further exemplified with reference to the following examples, which are presented for the purpose of illustration only and are not to be considered as limiting of the invention.

EXAMPLE 1

This example describes the step-by-step preparation and methods to render relatively inert amorphous calcium phosphate solids into a highly reactive amorphous calcium phosphate.

Solution A was prepared at room temperature by the rapid dissolution of 55 g $Na_2HPO_4.7H_2O$ (sodium phosphate), 50 g NaOH (sodium hydroxide), 30 g $NaHCO_3$, (sodium bicarbonate) in 1.3 l of distilled water. Solution B was prepared at room temperature by rapid dissolution of 43 g $Ca(NO_3)_2.4H_2O$ (calcium nitrate tetrahydrate) in 0.5 l of distilled water.

The inert carbonated amorphous calcium phosphate was then prepared at room temperature by the rapid addition of solution B to rapidly stirring solution A. The precipitate of gel-like amorphous calcium phosphate thus formed was immediately filtered using filter paper (0.05 sq. m) with medium filter speed and a vacuum pressure of about $10^{-2}$ torr. The material formed a thin cake and was washed with approximately 4 liters of distilled water by adding water into the filtrating funnel. The washed material was then collected using spatula and immersed into a liquid nitrogen in a 2.5 L container. Following the formation of hard frozen pieces, the container was transferred into a vacuum chamber for 24 hrs ($10^{-1}$–$10^{-2}$ torr), until a fine and dry powder was obtained.

Although the procedure described above may be performed at room temperature, the entire process preferably takes place below ambient temperature (4–5 ° C.), so as to further prevent the amorphous state from converting into more stable crystalline form. Further, in preferred embodiments, elements or ions known to act as inhibitors of crystalline hydroxyapatite formation may be added into the solution in trace amounts. For example, $Mg^{2+}$ ions in the form of less than 1.0 g $MgCl_2.6H_2O$ (magnesium chloride), pyrophosphate ions in the form of less than 2 g $Na_4P_2O_7.10H_2O$ (sodium pyrophosphate).

Figure 4A:
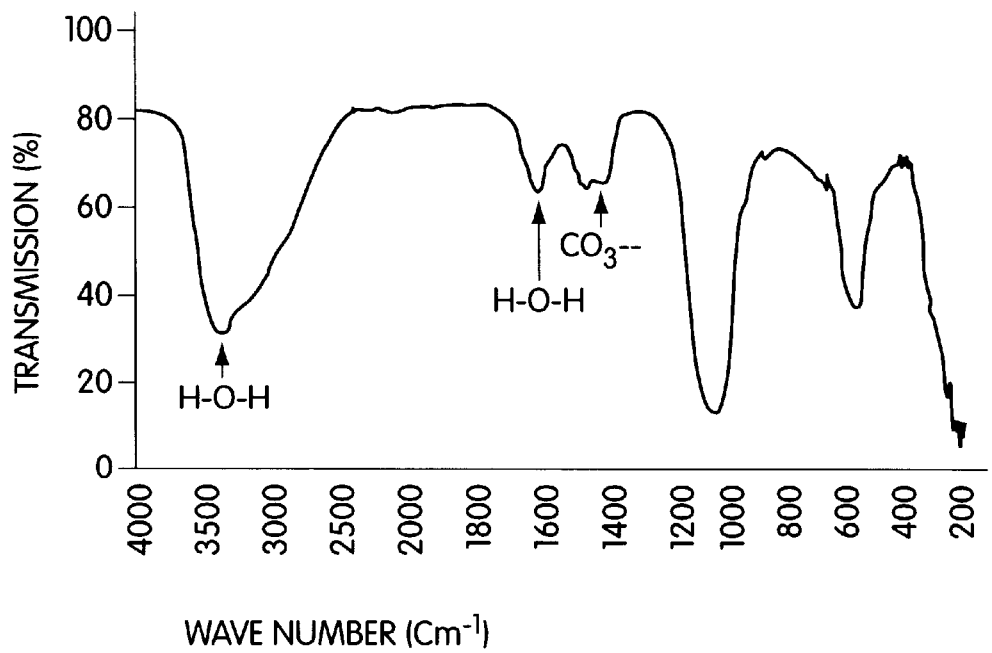
FIG. 4 shows infrared spectra of the reactive amorphous calcium phosphate of the present invention (a) prior to and (b) after heating step in which band intensities for the H—O—H group (~3,550 $cm^{-1}$ and 1,640 $cm^{-1}$) and $CO_3^{2-}$ group (1420–1450 $cm^{-1}$) are altered upon heat treatment.
Figure 4B:
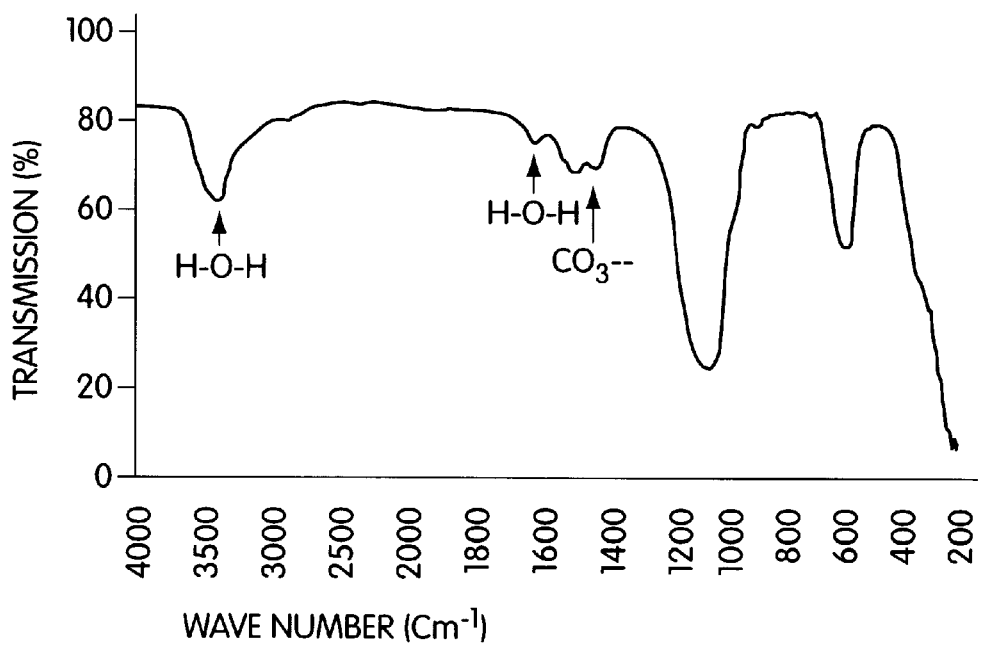

An infrared spectrum of the inert amorphous material at this point in the process is shown in FIG. 4(a). This spectrum contains peaks characteristic of P—O groups (600 and 1000 $cm^{-1}$), $CO_3^{2-}$ group (1,420–1,450 $cm^{-1}$) with relatively large peak of O—H group (~3,550 $cm^{-1}$). The inert amorphous material described above was then made into a reactive form by heating for 60 minutes at 450° C. (±3° C.). The IR of the heated material is shown in FIG. 4(b). This spectrum showed reduction of particular O—H and $CO_3^{2-}$ groups, indicating significant reduction of $H_2O$ and $CO_3^{2-}$ as $CO_2$ and $H_2O$. In similarly prepared samples the carbon content was observed to drop approximately 60% with a total carbonate ratio decreasing from 1.56% to 0.5%.

The overall morphological and ultrastructural properties of amorphous material is shown in FIG. 2, as seen under a transmission electron microscope. Note the "amorphous" appearance of the material with absence of sharp edges separating each granules with certain portion of the material to exhibit shapeless form (arrows). An extremely high specific surface area of 120 $m^2/g$, with an average pore size of approximately 130 Å was observed in this material.

EXAMPLE 2

This example describes the preparation of PCA calcium phosphate.

Dicalcium phosphate dihydrate (DCPD) used in this example was prepared in the following manner. Solution A was prepared at room temperature by rapid dissolution of 10 g $H_9N_2O_4P$ (diammonium hydrogen phosphate) in 500 ml distilled water at a pH of 7.8. Solution B was prepared at room temperature by the rapid dissolution of 17.1 g $Ca(NO_3)_2.4H_2O$ (calcium nitrate tetrahydrate) in 250 ml distilled water at pH of 5.5–6. The dicalcium phosphate dihydrate was prepared at room temperature by the rapid addition of solution B to the stirring solution A. Immediately thereafter, the sample was filtered using filter paper (0.05 sq. m) with medium filter speed and a vacuum pressure of about $10^{-2}$ torr. The material formed a thin cake which was washed with about 2 liters of distilled water and then dried at room temperature for 24–72 hrs.

The reactive amorphous calcium phosphate material prepared from Example 1 was physically dry-mixed with dicalcium phosphate dihydrate ($CaHPO_4.2H_2O$) at 50:50 wt % using a mortar and pestle for 3–5 min. Water (1 mL/g of mixed material) was then added to the powder mixture to yield a hydrated precursor of paste-like consistency. The amount of $H_2O$ added varied, depending on whether a thick or thin paste was desired. The paste material was then placed in a moist tissue environment which at 37° C. hardened into a solid mass without exothermic behavior. The hardening process could be delayed for several hours by placing it into a refrigerating temperature of 4° C. Also, hardening may proceed at ambient temperatures, although set-up (hardening) time may be increased.

Figure 5:
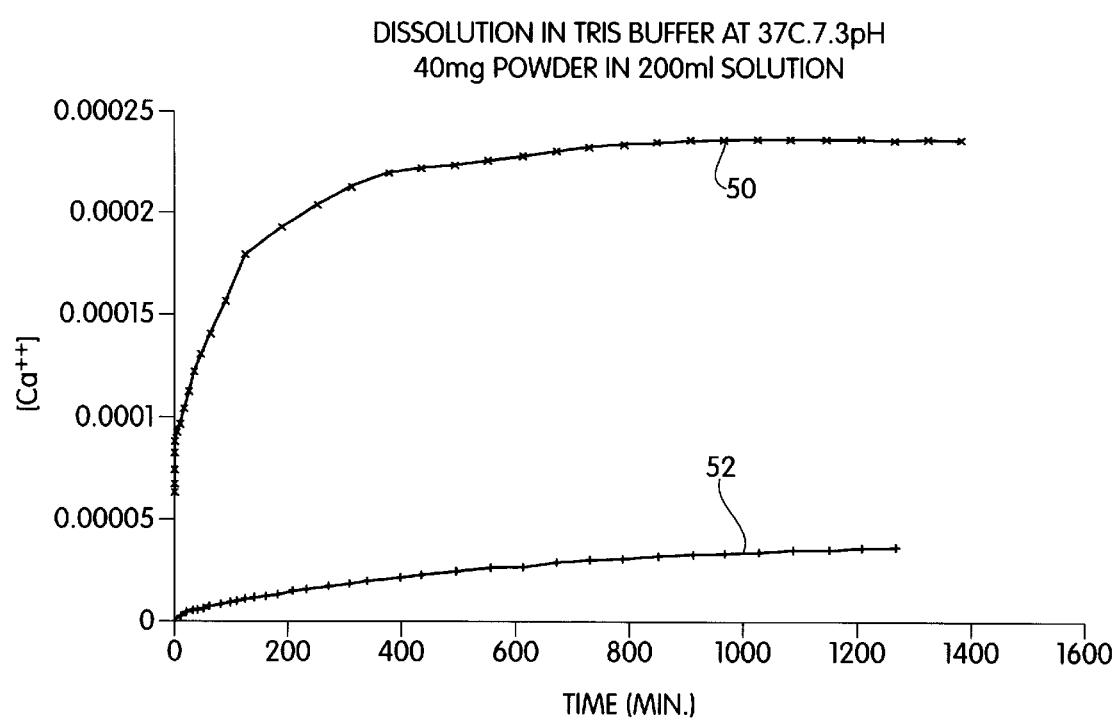
FIG. 5 is solubility curve of (a) a poorly crystalline apatitic calcium phosphate and (b) crystalline hydroxyapatite.

The hardened material was composed of nanometer-sized, poorly crystalline hydroxyapatite with an inherent solubility property that exceeded reported solubilities for a synthetic hydroxyapatite material. This is demonstrated in FIG. 5, where the concentration of calcium ions released into a controlled pH buffer solution over 24 hrs at 37° C., was significantly higher for the PCA calcium phosphate material of the present invention (curve 50) than the standard crystalline hydroxyapatite material (curve 52).

EXAMPLE 3

This example demonstrates the preparation of PCA calcium phosphate material using materials having a selected particle size.

The reactive amorphous calcium phosphate material prepared as in Example 1, was physically dry-mixed with dicalcium phosphate dihydrate ($CaHPO_4.2H_2O$) with a particle size of less than 100 $\mu$m at 50:50 wt. % using a SPEX 8510 laboratory mill for 2 min with a 8505 alumina ceramic grinding chamber, followed by sieving to a size of less than 100 $\mu$m. Water (1 ml/g of mixed material) was then added to the powder mixture to yield a paste-like consistency.

EXAMPLE 4

This example describes alternative methods for preparing a poorly crystalline apatitic calcium phosphate.

(a) Reactive ACP and DCPD were prepared as described in Examples 1 and 2. Water (0.8 ml) was added to ACP (0.5 g) and mixed thoroughly to homogeneity with a spatula to form a paste. 0.5 g of DCPD was then added to the paste and the paste was mixed for an approximated 2 min. The paste material was then placed in a moist tissue environment where upon reaching body temperature (37° C.), hardened into a solid mass without exothermic behavior.

(b) Reactive ACP and DCPD were prepared as described in Examples 1 and 2. Water (0.8 ml) was added to DCPD (0.5 g) and mixed thoroughly to homogeneity with a spatula to form a paste. 0.5 g of reactive ACP was then added to the paste and the paste was mixed for an additional 2 min. The paste material was then placed in a moist tissue environment where upon reaching body temperature (37° C.), hardened into a solid mass without exothermic behavior.

In both instances, the paste hardened after 30 minutes, indicating a successful reaction.

EXAMPLE 5

This example describes the preparation of PCA calcium phosphate using alternative second calcium phosphate sources. Both pre-hardened PCA calcium phosphate and crystalline hydroxyapatite reacted with reactive amorphous ACP to produce a PCA calcium phosphate.

(a) Poorly crystalline HA is prepared as described in U.S. Ser. No. 08/554,817 filed Nov. 7, 1995, incorporated herein by reference, using only carbonate as an inhibitor (no $Mg^{++}$ or pyrophosphate). The resultant powder was then lyophilized.

(b) Hydroxyapatite was obtained in powder form from Aldrich Chemicals (#28,939-6; lot 00325AQ).

Figure 6A:
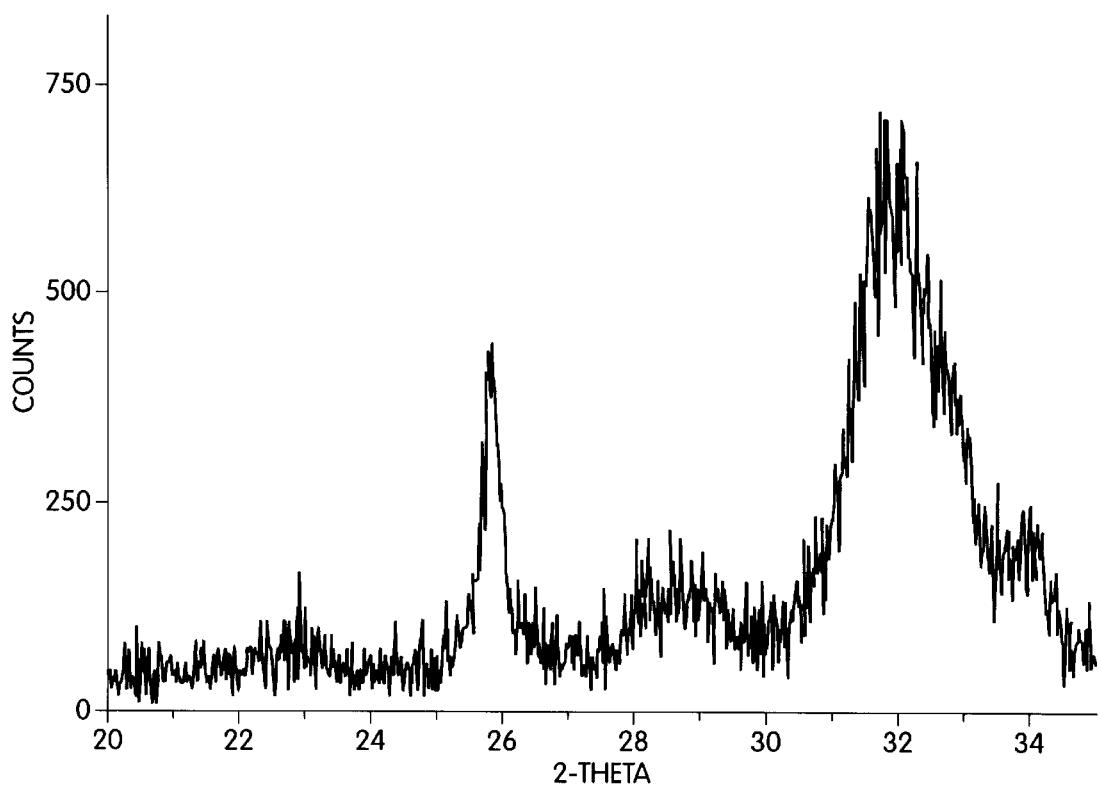
FIG. 6 is the X-ray diffraction pattern of a poorly crystalline apatitic calcium phosphate prepared using (a) a pre-hardened poorly crystalline apatitic calcium phosphate and (b) crystalline hydroxy apatite as the second calcium phosphate source.
Figure 6B:
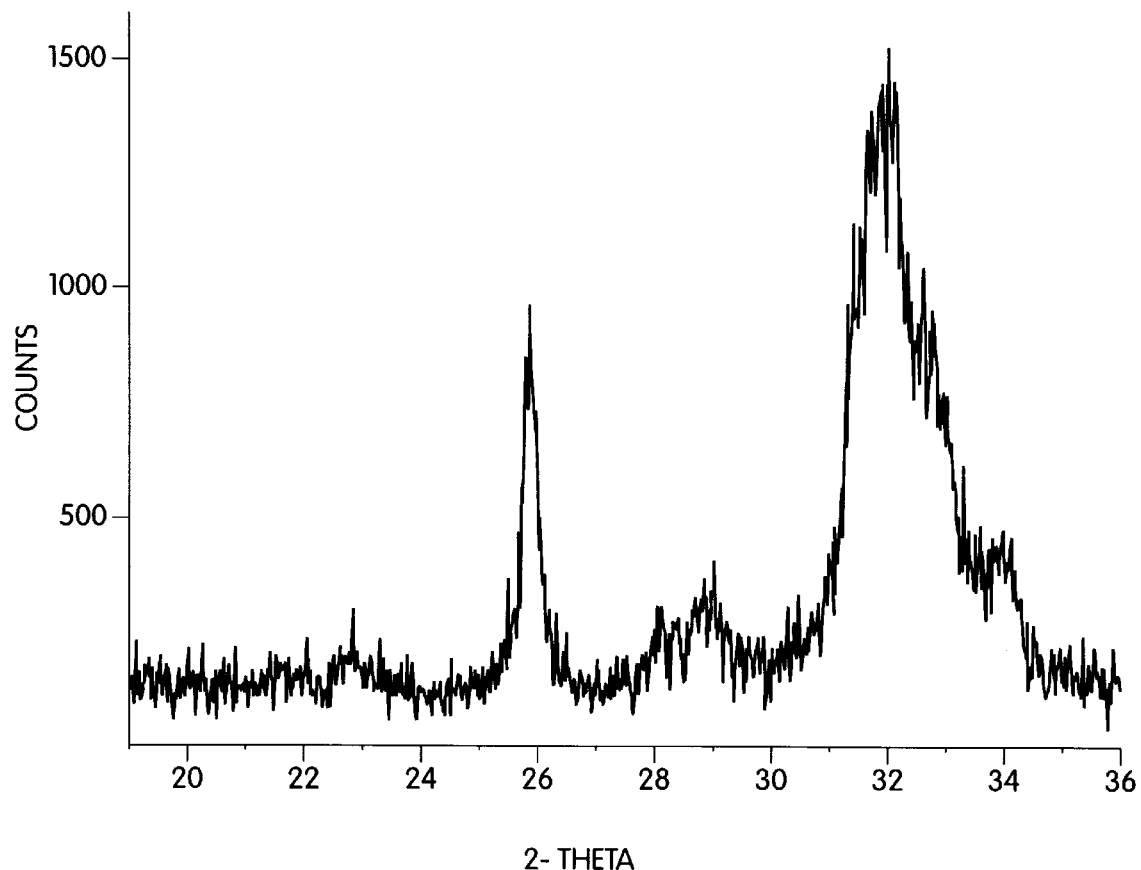

Each of the two powders was mixed 1:1 with reactive amorphous calcium phosphate, prepared as described in Example 1 and mixed with water. Both mixtures hardened within 30 minutes at 37° C. and IR spectra of the reaction products were substantially the same as that of the PCA calcium phosphate produced according to Example 2. XRD spectra are found in FIGS. 6(a) and 6(b), respectively.

EXAMPLE 6

This example describes the preparation of particulate PCA calcium phosphate which may be used in the composites of the invention.

Reactive amorphous calcium phosphate and DCPD are prepared as described in Examples 1 and 2 and are used to prepare poorly crystalline hydroxyapatite as described in Example 2. The hardened PCA calcium phosphate is lyophilized overnight and pulverized in a grinder and then passed through one or more sieves to obtain a desired particle size. Particles are then introduced into a PLGA matrix. A variety of composite matrices are prepared as follows:

(a) 25 μm average particle size PCA calcium phosphate (10% wt/wt) in PLGA;

(b) 25 μm average particle size PCA calcium phosphate (5% wt/wt) in PLGA;

(c) 100 μm average particle size PCA calcium phosphate (5% wt/wt) in PLGA; and (d) 200 μm average particle size PCA calcium phosphate (5% wt/wt) in PLGA.

The composites prepared as above are placed intramuscularly in a rodent and resorption rates determined according to Example 16A to identify composites suitable for use in resorbable bioceramic composites.

EXAMPLE 7

Characteristics of Injectable Paste for Formation of Synthetic PCA material from a reactive, amorphous calcium phosphate. These examples demonstrate the effect of fluid volume on the consistency and reactivity of injectable paste to be used in the formation of a synthetic, poorly crystalline hydroxyapatite material. Each of the pastes were prepared by mixing precursor powders to give a dry mixture Ca/P ratio of 1.5–1.7; and adding distilled water to form a putty or paste. The consistency and rate of reaction at room temperature and 37° C. were determined. Observations are reported in Table 1.

TABLE 1

| | Formability, injectability and reactivity of one gram hydrated precursor material prepared with variable water volume | | |
|---|---|---|---|
| Example No. | water volume (mL) | formability | injectability | hardening time (min) (4 *C/RT/37° C.) |
| 7-1 | 0.7 | – crumbles | – | –/–/– |
| 7-2 | 0.8* | +++ easily formed paste | + | >60/>60/30 |
| 7-3 | 0.9* | ++ toothpaste | ++ | >60/>60/30 |
| 7-4 | 1.0 | + liquid toothpaste | +++ | >60/>60/30 |

*Under some circumstances (e.g., evaporation) these samples may dry out somewhat over a period of one hour at room temperature. In such cases, additional water may be added to restore the original consistency.

EXAMPLE 8

This example describes hardness testing of a PCA calcium phosphate and its composites.

PCA calcium phosphate was prepared according to Examples 1 and 2 to form a paste. The paste was placed into a 6×10 mm hollow Teflon® tube submersed in 37° C. water for 30 minutes. The hardened PCA calcium phosphate was then removed from the tube and placed in water at 37° C. for 1 hour and then, while still moist, placed vertically on an Instron 4206 having a dual load 10 Kg/15 ton load cell. Compressibility was determined using a crush test. Approximately, 200–250 N were required to bring the sample to failure. This force corresponds to a compressive strength of 7–9 MPa.

Poly(lactide) whiskers are prepared with average dimensions of about 5–100 μm diameter by 10–250 μm length. The whiskers are mixed with poorly crystalline hydroxyapatite paste prepared as described above at a concentration 10% wt/wt. The composite paste is hardened overnight at 37° C. in a moist environment. When tested for compressibility, the composite is found to have improved compressibility over the non-composite PCA calcium phosphate.

EXAMPLE 9

This example describes the preparation and testing of resorbable PCA calcium phosphate composites.

A PCA calcium phosphate/poly(lactide) composite paste is prepared as described in Example 6 or Example 8. The paste is packed into molds in the shape of intermedulary nails, support plates, and screws. The molds are heated to 37° C. for three hours in a moist environment and the hardened objects are removed from the mold. The composite objects are implanted into animal models according to the procedure set forth in Example 18, in all cases being sure to contact the object with bone forming cells. Composites which are found to be fully resorbed and ossified in less than 6 months are suitable for use as bioresorbable bioceramic composite implants.

EXAMPLE 10

This example describes a resorbable composite for use as a bone filler or cement. A PCA calcium phosphate/dextran composite may be prepared by first preparing the paste as described in Example 2. The paste may be well mixed with 10% vol/vol polydisperse dextran, hardened in a moist environment and shown to have improved strength and compressibility. The hardened composite may be then introduced into a fracture site in an animal model according to Example 18. The time for resorption and reossification are determined. Screening according to Example 11 is used to determine the suitability of the composite as a resorbable bioceramic implant.

EXAMPLE 11

This example describes the coating of PCA calcium phosphate particles with a biodegradable outer coating. Particles prepared in this way resorb and/or ossify with an initial delay period as compared to PCA calcium phosphate alone.

PCA calcium phosphate particles may be prepared as described in Example 2. The particles may be prepared in a series of homogeneous lots with average particle sizes in the range of 60–100 microns according to the method used in Example 3. These particles may be then uniformly dip coated with poly(lactide). The coated particles are placed intramuscularly in order to evaluate the resorption kinetics, which may be delayed as compared to uncoated particles.

EXAMPLE 12

This example describes the use of a PCA calcium phosphate/hydroxyapatite composite to produce new bone. This form of bone is useful in augmentation therapy.

Crystalline hydroxyapatite may be prepared or obtained as 50–200 micron particles. These particles may be introduced into a PCA calcium phosphate paste at approximately 1 to 50 wt % and may be well mixed. The resultant composite paste may be formed into the desired shape, seeded with bone forming cells and implanted adjacent to cortical bone and fixed by suturing and soft tissue approximation. The composite may also be seated on a recipient bone which has been surgically fashioned according to the method of Example 18. After three months, the implant site may be examined as in Example 18 to establish that the new bone impregnated with particulate hydroxyapatite is formed in the shape of the formed implant.

EXAMPLE 13

This example describes the formation of a PCA calcium phosphate composite with a lubricant.

A PCA calcium phosphate paste may be prepared according to Example 2. Silicone oil may be mixed with the paste at a concentration in the range of 0.1 to 30 wt %. Before the hardening reaction occurs, the paste may be injected through a 16–22 gauge needle and found to have significantly improved injectability as compared to an untreated paste.

EXAMPLE 14

This example demonstrates the use of a PCA calcium phosphate composite to embed an object in the recipient's bone. In addition to placement of anchoring devices, similar approaches can be used to embed almost any desired agent into a recipient's bone, including but not limited to support rods and fibers, imaging agents and friction reducing substances such as teflon plates.

A dacron loop approximately 1 mm in diameter may be formed on a 2 cm dacron suture. A knot may be placed within the suture approximately 2 mm from the loop. The suture may be then trimmed at the knot, leaving a loop with a 2 mm knotted tail. A 1 mm diameter hole may be drilled approximately 3 mm into a recipients's bone. The knotted end of the suture may be placed within the hole and the hole may be then filled with PCA calcium phosphate paste. After six months, suture site is evaluated for resorption of the PCA material in order to evaluate the composite's suitability as a resorbable bioceramic composite.

The procedure may be repeated in a second subject with the following modification. Following placement of the knotted suture within the hole, a prehardened PCA calcium phosphate plug may be wedged securely into the hole, thereby mechanically securing the suture in place. The hole may be then sealed with poorly crystalline hydroxyapatite paste. After six months, suture site is evaluated for resorption of the PCA material in order to evaluate the composite's suitability as a resorbable bioceramic composite.

EXAMPLE 15

Implantation and Resorption of PCA calcium phosphate in a Bony Site. The purpose of this study was to assay resorption and ossification of PCA calcium phosphate in a bony implant site. The method is also useful for testing the resorption and ossification properties of PCA calcium phosphate formulations and composites of the invention.

The test article used was a PCA calcium phosphate formulation prepared as described in Example 2. The ACP and DCPD were mixed in the specified proportions and ground for 1 minute, 30 seconds in the SPEX grinder equipment.

Adult (>5 month old) NZW male rabbits were held in quarantine and acclimatized for a minimum of 10 days prior to the initiation of the study. Animals were individually housed in suspended stainless steel cages. Wood shavings were used in dropping pans under the cages. Prior to initiation of the study, animals were assigned to groups or treatments randomly and were identified by a numbered ear tattoo and by a corresponding cage card. All animals had single defects placed in one tibia. Timepoints for evaluations were 2, 4, and 8 weeks (2 animals at each timepoint). Surgery was performed under full anesthesia and aseptic surgical conditions.

After obtaining adequate anesthesia (e.g., ketamine/xylazine to effect), using aseptic technique, an incision was made over the lateral proximal tibia. The soft tissue was deflected away and the bone exposed. Using an approximately 5 mm trephine in a low speed dental handpiece with irrigation (0.9% physiologic saline) as needed, a ~5.5 mm diameter hole was cut through the cortical portion of the bone. The bony disk was dissected free from the cortex and the site was prepared for implantation. The hydrated precursor material in paste form was placed into the defect. Defects in control animals were left untreated. The soft tissues were then closed in layers. One sample per animal was prepared using this method.

Clinical observations of the animals' general health and well-being, with special regard to their ambulatory abilities, were made at least weekly. All animals appeared to be in good health. At the end of the study the animals were euthanized with an overdose of anesthetic and the implant site collected. Radiographs of the tibiae were made at scheduled intervals including after surgery and at the time of necropsy.

The implantation sites were fixed in formalin and stained with either hematoxylin and eosin, Masson's trichrome, or Von Kossa stained slides from decalcified samples. Undecalcified histological samples were also prepared and stained with light green basic fuschin. Slides were microscopically evaluated by a board certified veterinary pathologist (ACVP) with experience in laboratory animal pathology.

Subjective observations were made of bone morphology, and presence or absence of organized bone and of detectable PCA calcium phosphate material was noted.

Figure 7A:
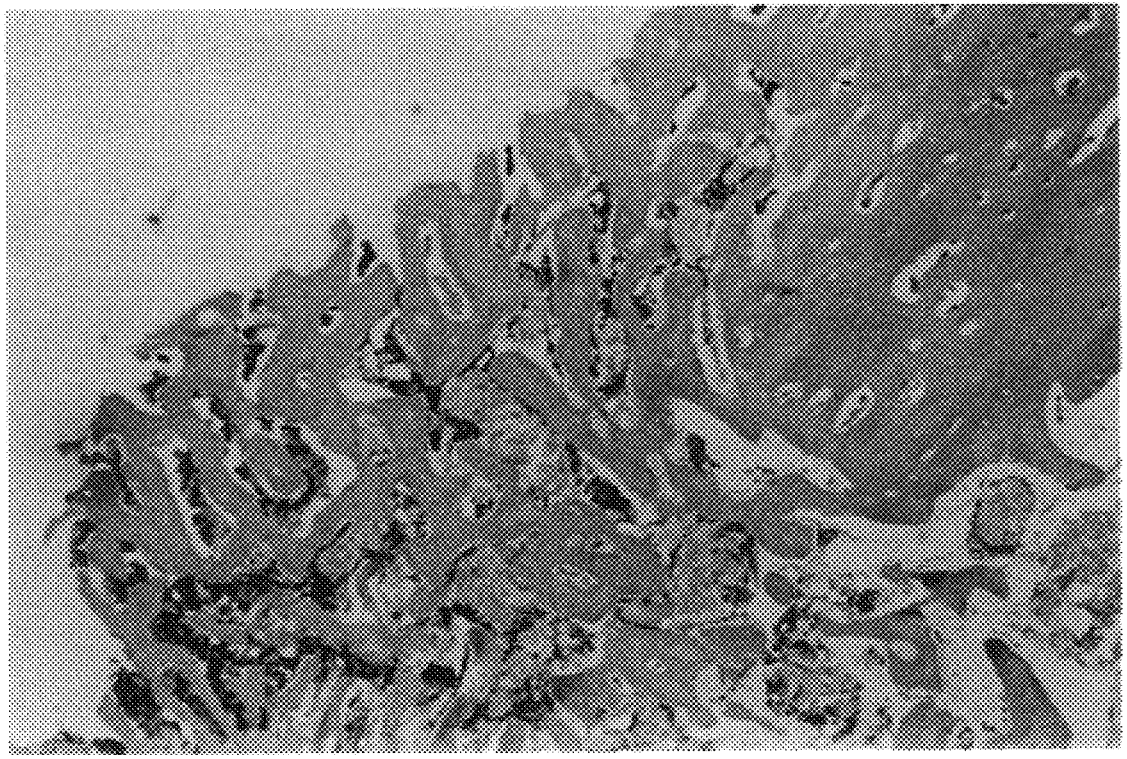
in FIG. 7a, the small arrows indicate one edge of the defect; the large arrowhead is at the yet unbridged defect.
Figure 7B:
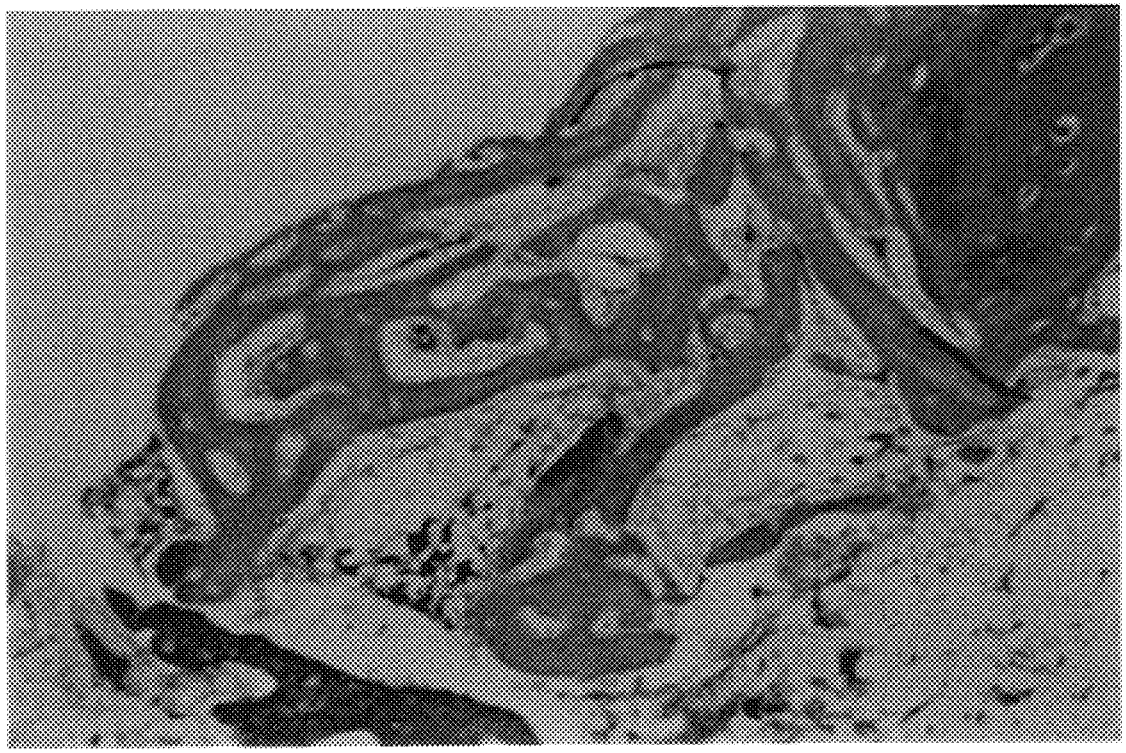
in FIG. 7b, large arrowheads denote one edge of the defect. In both figures, magnification is 4×, bone is decalcified, and slides are treated with hematoxylin and eosin.

Histological results indicated some mineralization at 2 weeks. By 4–6 weeks, animals receiving implants had normal trabecular bone at the implant site with no evidence of remaining PCA calcium phosphate. The untreated controls had not fully healed in that they had less than full ingrowth and/or had non-cortical-type bone. FIGS. 7a and 7b are photomicrographs of untreated and treated tibia defects, respectively, 2 weeks after surgery. As can be seen, bone to the right of the defect edge in the untreated sample (FIG. 7a) is thin trabecular bone; new bone to the right of the defect edge in the treated sample is thick trabecular bone.

EXAMPLE 16

Implantation and Resorption of PCA calcium phosphate in a Subcutaneous Site. This example demonstrates the resorption of the inventive PCA calcium phosphate when implanted subcutaneously into rats. It also demonstrates a useful screening procedure to test resorption characteristics of new formulations of bioceramic implant materials and composites.

Eighty male and eighty female Sprague-Dawley rats were each implanted with 4 ml (2–4 gm) of the inventive PCA (prepared according to Example 4) into the dorsal subcutis (>10x the amount considered maximal in humans on a per kg basis). Control animals were treated with an equal volume of saline. Operation procedures are described in Example 16A. The rats were sacrificed according to the schedule presented below in Table 2; the implant site was examined as described in Example 16.

TABLE 2

Sacrifice Schedule

| Sacrifice Timepoint | PCA calcium phosphate implant |
| --- | --- |
| 1 week | 5 m/5 f |
| 2 weeks | 5 m/5 f |
| 1 month | 5 m/5 f |
| 3 months | 5 m/5 f |
| 1 year | 20 m /20 f |

Blood for clinical pathology analyses was collected via retroorbital sinus or cardiac puncture (all by the same method) while the animals were under $CO_2$ anesthesia. Blood samples were collected from each group of animals prior to scheduled sacrifice. Clinical observations of the animals for general health and well-being were performed at least weekly until 3 months, and then monthly.

At 1 week PCA material was present at the implant site and was found associated with moderate to marked granulomas presumable associated with the resorption process. At week two a small amount of PCA material was still present at the implant site and associated granulomas were mild to moderate. By week four most tissue appeared normal with a few mild granulomas persisting at the implant site. At week twelve no evidence of the implant remained.

EXAMPLE 16A

Implantation and Resorption of PCA calcium phosphate in an Intramuscular Site. This example describes the preparation of PCA material that have varied in vivo resorption times as a result of varied grinding times. Individual dry precursors, ACP and DCPD were prepared as described in Example 4. Several different formulations of DCPD and ACP were then prepared by i) grinding DCPD for 15 sec, 30 sec, 1 min, 2.5 min, or 5 min in a SPEX grinder; ii) combining the ground DCPD 1:1 with ACP; and iii) grinding the mixture for an additional 15 sec, 30 sec, 1 min, 2.5 min, or 5 min, respectively. Total grinding times for the different preparations were therefore 30 sec, 1 min, 2 min, 5 min, and 10 min.

The PCA calcium phosphate, sterilized in powder form by approximately 2.5 Mrad of gamma irradiation, was prepared as described in Example 2 by taking the material in powder form and mixing with sterile water or saline and forming it into approximately 1 cm disks 2 mm thick and incubated for a minimum of 30 minutes at 37° C. Disks were implanted into adult male New Zealand White Rabbits immediately following fabrication.

Animals were assigned to dose groups which contained 3 males for a total of 15 animals. The implants were assigned to the rabbits randomly. 10–15 minutes prior to the surgery, the animal was premedicated with xylazine (10 mg/kg, i.m.). The animal was then given ketamine (50 mg/kg, i.m.). The dorsal surface of the animal was clipped free of hair and washed with a betadine surgical solution and alcohol. Before the surgery the animal was monitored to be sure that is was properly anesthetized. To do this, pressure was applied to the foot pad. When there was no response, the animal was properly anesthetized. Throughout the procedure, the animal was monitored for whisker twitching and the toe-pinch reflect, which indicated that the animal was not waking up.

Using aseptic technique and a scalpel blade, an incision 1–2 cm in length was made in the skin over the m. longissimus lumborum (which lies along both sides of the spine). When the incision was made, the underlying fascia and muscle was also cut to allow the sample to pas into the muscle. The sample disk was placed directly into the muscle, being sure that the entire implant was embedded in the muscle. The muscle was closed with a single absorbable suture and the skin was stitched closed subcutaneously. Metal skin staples were used to close the external skin surface incision. Five samples were placed on each side in this manner. Each sample was placed at the end of the incision and they were approximately 1 cm apart from each other (see diagram). The samples were in the form of 7 mm by 2 mm disks weighing approximately 150 mg. The animals were monitored and were given buprenorphine (0.02–0.05 mg/jg, s.q) upon awakening. The analgesic was administered 2 times per day for three days after surgery.

The animals were radiographed immediately after the surgery and for every two weeks thereafter. The radiographs were compared to track the resorption of the materials. A standardized method was used for the radiographs to minimize any variation between timepoints.

After euthanasia, implant sites were first evaluated by gross examination. In those sites with visible implants, the implants appeared as grey to yellow solid discs. In those sites where the implant had been resorbed, areas of red to tan discoloration of the muscle were observed.

Muscle tissue, with the implants, was removed, being careful not to disturb the implants. The tissues and the identifying marks were placed into labeled jars filled with 10% neutral buffered formalin. All implant sites were processed and evaluated microscopically. Observations included focal fibrosis, focal granulomatous inflammation, and appearance of the implant (in some cases). Fibrosis was primarily seen as fibrocytes and collagen. Animals with gross resorption had fibrosis and minimal to moderate granulomatous focal inflammation. Granulomatous inflammation was seen as focal aggregates of macrophages and giant cells, often with intracytoplasmic crystals, and occasional heterophils and lymphocytes. Inflammation around the non-resorbed implants was primarily minimal to mild fibrosis and/or granulomatous inflammation, both of which are within the acceptable range for intramuscular implants.

At four weeks, the pellets made from PCA calcium phosphate implants that had been prepared by grinding for 30 seconds, 1 minute, or 2 minutes were fully resorbed. Those that had been prepared by grinding for 5 minutes or 10 minutes were not fully resorbed.

EXAMPLE 17

Implantation and Resorption of PCA calcium phosphate in a Bony Site. The purpose of this study was to assay resorption and ossification of the PCA calcium phosphate of the invention in a bony site.

Mature (>1 year) beagle dogs were employed for this study because of their size and historical use as a model for bone studies. The tibia of the dog is large enough to allow large (>5 mm) defects to be created and studied without compressing the ability of the animal to ambulate without inducing fractures secondary to induction of defects in the bones.

Ten adult male and female beagle dogs (6.0–15.0 kg) received the same treatment; Defects were created in the lateral surface of the tibial crest cortex (8 mm or 10 mm) in each tibiae. PCA calcium phosphate was placed in the defect in one tibia and the other tibia served as a control.

An incision was made over the proximal tibia. The soft tissue was deflected away and the bone was exposed. Using an 8 mm trephine in a low speed dental handpiece with irrigation (0.9% physiologic saline) as needed, the bony disk was dissected free and the site was prepared for implantation. The inventive calcium phosphate material (solid or paste) was placed into the defect. The soft tissues were then closed in layers. One to three samples per animal were performed using this method. The animals were allowed to heal for scheduled periods of time.

Animals were assessed by clinical observations, radiographs, and microscopy of the defect sites at 0, 2, 4, and 8 weeks. Specifically, tibia radiographs were taken every 2 weeks throughout the study. The radiographs were used to determine the duration of the study. Approximately at the end of every 2 weeks, 2 animals were sacrificed and the test sites were removed for histology. The implantation sites were prepared as undecalcified and decalcified sections.

Two dogs were used as pilot animals and did not receive and PCA material. In these pilot animals, some healing was observed radiographically at 2 weeks. By 6–8 weeks, the defect was completely healed. The size of dog defects was determined to be optimal at 1 cm. In the remaining 8 dogs, control defects healed within 6 weeks; treated defects healed in 2 to 4 weeks. The quality of the bone in the control defects was thin trabecular bone; in the treated defects, the bone was thick trabecular to cortical type bone. Thus, the treated defects healed approximately 2 weeks faster than did untreated defects, and healed with better bone thickness.

Figure 8:
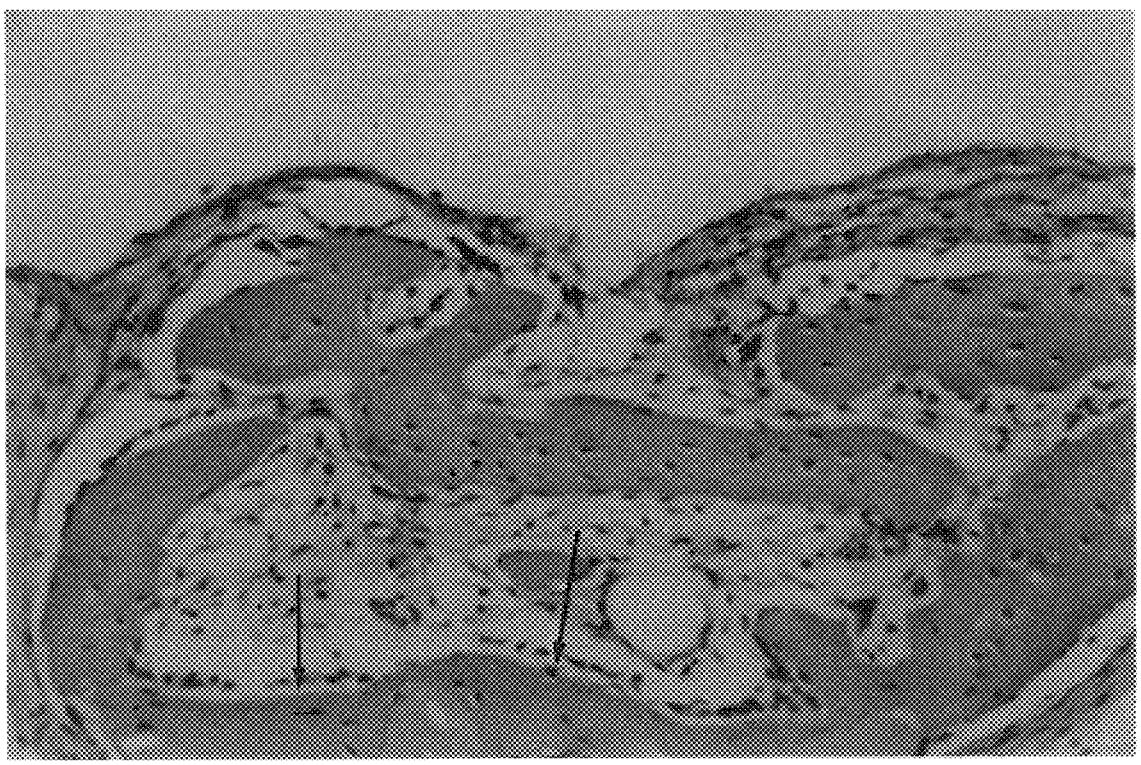
FIG. 8 is a photomicrograph of canine trabecular bone grown into a defect treated with the PCA calcium phosphate of the present invention 8 weeks after surgery (magnification 10×; decalcified; hematoxylin and eosin)

FIG. 8 shows a highly magnified (10x) photograph of canine trabecular bone growth into a defect site treated with the PCA material of the invention 8 weeks after surgery. The small arrows denote osteoblast-like cells lining the bone spicules and are indicative of enhanced cellular activity.

Figure 9:
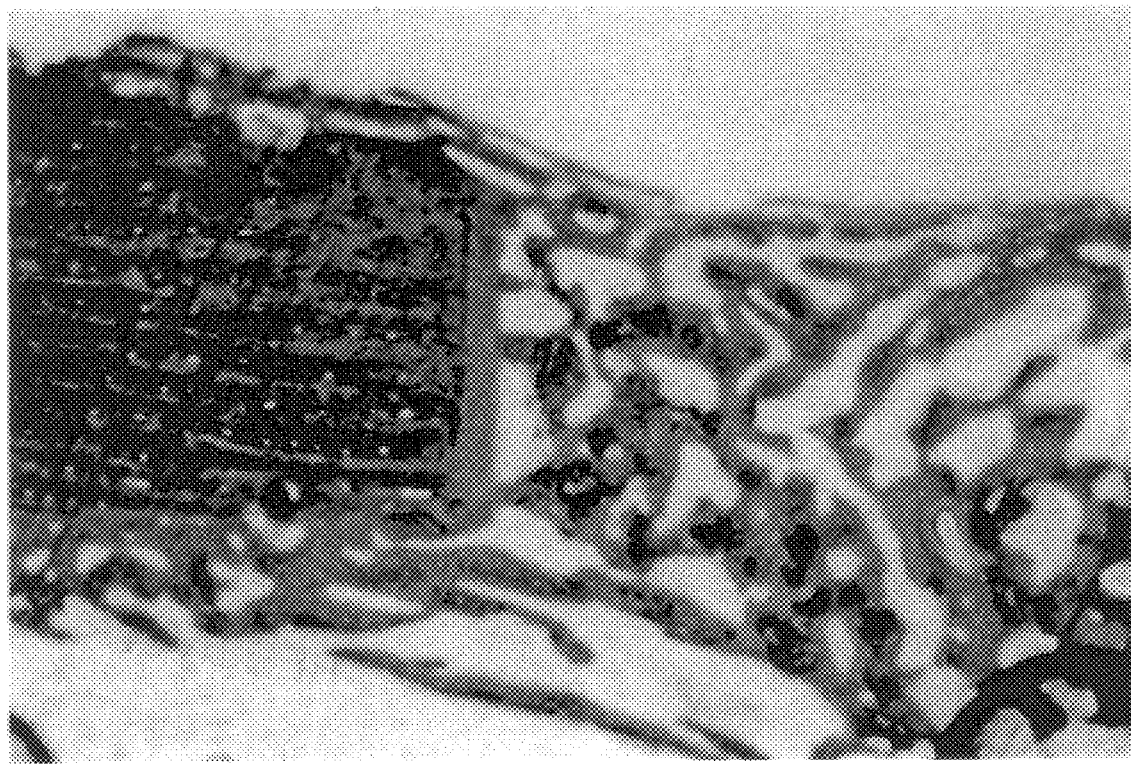
FIG. 9 is a photomicrograph of a canine cortical bone defect that was treated with the PCA caclium phosphate of the present invention 4 weeks after surgery (magnification 4×; undecalcified, Light Green Basic Fuchsin)

FIG. 9 shows a photomicrograph of a canine cortical bone defect treated with the PCA material of the invention. The large arrows indicate one edge of the defect. The new bone growth is to the right of the defect; at 4 weeks after surgery, this growth is thick trabecular bone.

EXAMPLE 18

Implantation and Resorption of PCA calcium phosphate in a Bony Site. The purpose of this study was to assay resorption and ossification of the PCA calcium phosphate of the invention, and to establish parameters for screening test PCA calcium phosphate materials.

Eighteen adult (>3 month old) NZW male rabbits were used in these studies. After obtaining adequate anesthesia (e.g., ketamine/xylazine to effect), using aseptic technique, an incision was made over the proximal tibia. The soft tissue was deflected away and the bone was exposed. Using an approximately 5 mm trephine in a low speed dental handpiece with irrigation (0.9% physiologic saline) as needed, the bony disk was dissected free and the site was prepared for implantation. The inventive PCA calcium phosphate material (solid, granules or paste) was placed into the defect. The soft tissues were then closed in layers.

Clinical observations of the animals general health and well-being, with special regard to ambulation, were performed weekly and in more detail at the time of the bi-weekly radiographs. Radiographs of the tibiae were made at scheduled intervals including after surgery and at the time of necropsy.

The implantation sites were prepared as hematoxylin & eosin, Masson's trichrome decalcified samples and as undecalcified slides.

Findings and clinical observations were associated with surgery and were not associated with the PCA calcium phosphate implants. Postsurgical clinical observations were within the range of anticipated findings for surgery-related trauma. Radiographs were taken immediately postsurgery and at each scheduled sacrifice timepoint.

Immediately after surgery, all bone defect sites were distinct; implants appeared to have the same radiodensity as bone. At 2 weeks postsurgery, control defects had distinct sites and implant sites were less distinct and blended into surrounding bone; similar findings were observed at 4 weeks. At 7 weeks, all sites appeared similar with increased radiodensity. Grossly, defect sites at 2 weeks were visible clearly in control and treated animals. At 4 weeks and greater, the implant or control sites could not be grossly ascertained.

Radiographic findings indicated little change in the control animals until week 7; animals treated with inventive PCA material had increasing radiodensity in the defect over time. Defects in control animals had some new bone ingrowth, predominantly of the thin trabecular type, within 4–7 weeks. Defects in treated animals had bone ingrowth as early as 2 weeks and by 7 weeks were filled with new bone. Microscopic findings are consistent with enhanced bone replacement with PCA calcium phosphate implants. Taken together, this study shows that 5 mm defects in rabbit tibia heal or have new bone growth in control animals by 7 weeks and in animals treated with the inventive PCA material by 4 weeks. Also, this rabbit unicortical 5 mm critical sized defect model is useful to analyze test articles for there resorptive and ossificative properties.

Figure 10A:
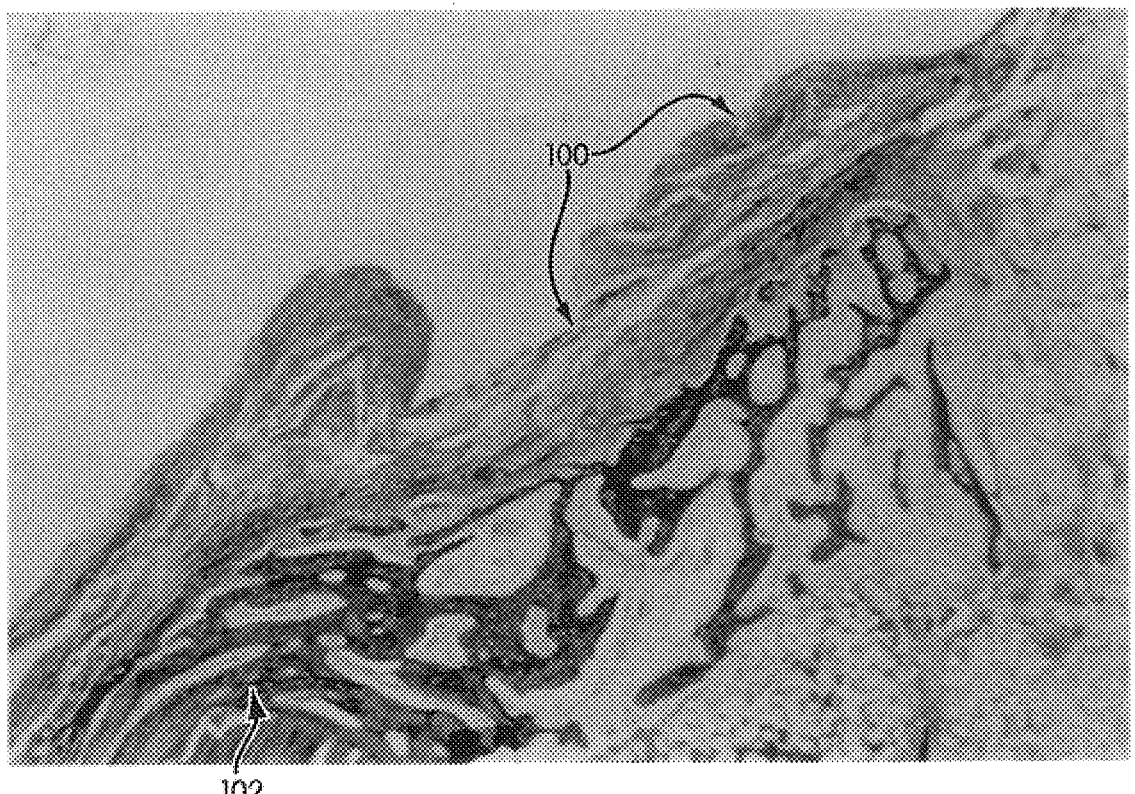
FIG. 10 presents photomicrographs of untreated (FIG. 10a) and treated (FIG. 10b) rabbit tibia defects 4 weeks after surgery (magnification 4×; decalcified; Masson's Trichrome).
Figure 10B:
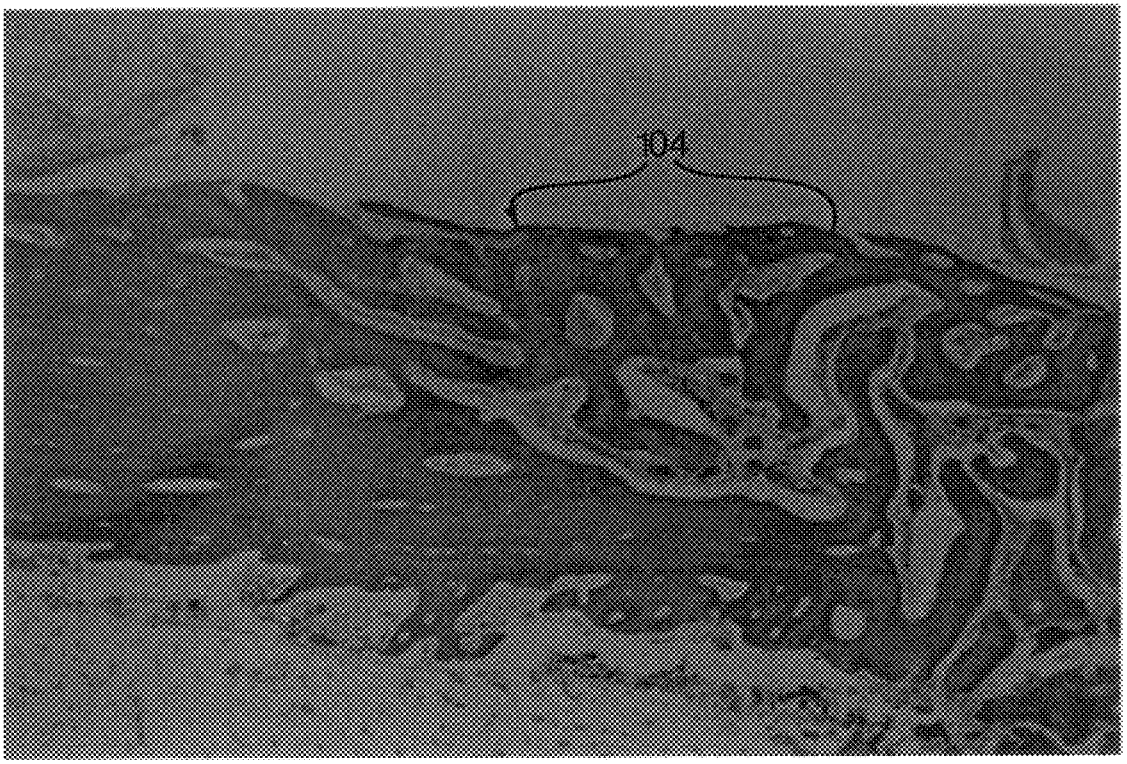

FIG. 10 shows photomicrographs of untreated FIGS. 10(a) and 10(b) and treated rabbit tibia defects 4 weeks after surgery. The large arrow indicates the edge of the defect. In FIG. 10(a), small arrows 100 denote an abundance of fibrous connective tissue on the defect site. The large arrowhead 102 points to new trabecular bone in the defect. In FIG. 10(b), the two small arrows 104 demarcate the thick trabecular bone growth in the defect site.

OTHER EMBODIMENTS

It will be understood that the foregoing is merely descriptive of certain preferred embodiments of the invention and is not intended to be limiting thereof. The following claims cover all of the generic and specific features of the invention herein described in the text and accompanying drawings.

What is claimed is:

1. A composite material, comprising:
    (a) a strongly resorbable, poorly crystalline apatitic (PCA) calcium phosphate cement having an x-ray diffraction pattern similar to naturally occurring bone made by the process comprising:
        providing a paste comprised of amorphous calcium phosphate and water, whereby the paste hardens and converts to the poorly crystalline apatitic calcium phosphate,
        the poorly crystalline apatitic calcium phosphate characterized in that, at least about 80% is resorbed within one year when 1 g of the PCA calcium phosphate is placed in a rat intramuscular site; and
    (b) a biocompatible supplemental material, said material in intimate contact with the poorly crystalline material and present in an amount effective to impart a selected characteristic to the composite.

2. The material of claim 1, characterized in that, said paste, when prepared from a reaction of amorphous calcium phosphate and a second phosphate in a fluid, the reaction mixture is injectable and formable for a time greater than about 30 minutes at about 25° C., and hardens within about 10 to 60 minutes at about 37° C.

3. The composite of claim 1, wherein the strongly resorbable, poorly crystalline apatitic calcium phosphate has an X-ray diffraction pattern comprising broad peaks at $2\theta$ values of 26°, 28.5°, 32° and 33°.

4. An orthopedic device comprising the composite of claim 1.

5. A bone cement comprising the composite of claim 1.

6. A method for embedding a supplemental material at a bony site, comprising:
    providing a strongly bioresorbable, poorly crystalline apatitic calcium phosphate having an x-ray diffraction pattern similar to naturally occurring bone, the poorly crystalline apatitic calcium phosphate made by the process comprising:
        providing a paste comprised of amorphous calcium phosphate and water, whereby the paste hardens and converts to the poorly crystalline apatitic calcium phosphate,
    said poorly crystalline apatitic calcium phosphate material in intimate contact with a non-resorbable or weakly resorbable supplemental material to form a composite;
    introducing the composite to a bony site, whereby the poorly crystalline apatitic calcium phosphate is resorbed and ossified and the non-resorbable supplemental material remains at the bone site.

7. The composite of claim 1, wherein the poorly crystalline apatitic calcium phosphate is characterized in that, at least about 80% of the poorly crystalline apatitic calcium phosphate is resorbed within nine months when 1 g is placed in a rat intramuscular site.

8. The composite of claim 1, wherein the poorly crystalline apatitic calcium phosphate is characterized in that, at least about 80% of the poorly crystalline apatitic calcium phosphate is resorbed within six months when 1 g is placed in a rat intramuscular site.

9. The composite of claim 1, wherein the poorly crystalline apatitic calcium phosphate is characterized in that, at least about 80% of the poorly crystalline apatitic calcium phosphate is resorbed within three months when 1 g is placed in a rat intramuscular site.

10. The composite of claim 1, wherein the poorly crystalline apatitic calcium phosphate is characterized in that, at least about 80% of the poorly crystalline apatitic calcium phosphate is resorbed within one months when 1 g is placed in a rat intramuscular site.

11. The composite of claim 1, wherein the supplementary material is bioresorbable.

12. The composite of claim 11, wherein the resorbable supplementary material is selected from the group consisting of collagen, demineralized bone matrix, hyaluronic acid and derivatives thereof, polyanhydrides, polyorthoesters, polyglycolic acid, polylactic acid, and copolymers thereof, polyesters of $\alpha$-hydroxycarboxylic acids, poly(L-lactide) (PLLA), poly(D,L-lactide) (PDLLA), polyglycolide (PGA), poly(lactide-co-glycolide (PLGA), poly(D,L-lactide-co-trimethylene carbonate), and polyhydroxybutyrate (PHB), polyanhydrides, poly(anhydride-co-imide) and co-polymers thereof, and bioactive glass compositions.

13. The composite of claim 1, wherein supplementary material is non-bioresorbable.

14. The composite of claim 13, wherein the non-bioresorbable supplementary material is selected from the group consisting of dextrans, polyethylene, polymethylmethacrylate (PMMA), carbon fibers, polyvinyl alcohol (PVA), poly(ethylene terephthalate)polyamide, bioglasses, calcium sulfate and calcium phosphates.

15. The composite of claim 1, wherein the supplementary material is a lubricant.

16. The composite of claim 15, wherein the lubricant is selected from the group consisting of silicone oil, polymer waxes, lipids and fatty acids.

17. The composite of claim 1, wherein the supplementary material is in the form selected from the group consisting of foam, sponge, mesh, particles, fibers, gels and filaments.

18. A method for embedding a supplemental material at a bony site, comprising:
    providing a paste comprised of amorphous calcium phosphate and water, whereby the paste hardens and converts to a poorly crystalline apatitic calcium phosphate,
    the poorly crystalline apatitic calcium phosphate having an x-ray diffraction pattern similar to naturally occurring bone, said poorly crystalline apatitic calcium phosphate material in intimate contact with a non-resorbable or weakly resorbable supplemental material to form a composite; and
    introducing the composite to a bony site, whereby the poorly crystalline apatitic calcium phosphate is resorbed and ossified and the non-resorbable supplemental material remains at the bone site.

19. The method of claim 6 or 18, wherein the paste remains injectable and formable for a time greater than about 30 minutes at about 25° C.

20. The method of claim 19, wherein the paste hardens at the bone site within about 10 to 60 minutes at about 37° C.

21. The method of claim 6 or 18, wherein the poorly crystalline apatitic calcium phosphate is resorbed such that when the composite comprises at least 1 g of poorly crystalline apatitic calcium phosphate, at least about 80% of the poorly crystalline apatitic calcium phosphate is resorbed within one month when the composite is placed in a rat intramuscular site.

22. The method of claim 6 or 18, wherein the poorly crystalline apatitic calcium phosphate is resorbed such that when the composite comprises at least 1 g of poorly crystalline apatitic calcium phosphate, at least about 80% of the poorly crystalline apatitic calcium phosphate is resorbed within six months when the composite is placed in a rat intramuscular site.

23. The method of claim 6 or 18, wherein the poorly crystalline apatitic calcium phosphate is resorbed such that when the composite comprises at least 1 g of poorly crystalline apatitic calcium phosphate, at least about 80% of the poorly crystalline apatitic calcium phosphate is resorbed within one year when the composite is placed in a rat intramuscular site.

24. The composite of claim 15, wherein the lubricant in present in an amount in the range of about 0.1–30 wt %.

25. The composite of claim 1, wherein the supplementary material comprises a radiographic material.

26. The composite of claim 17, wherein the supplemental material is in the form of a fiber and the fiber is present in an amount in the range of about 0.01–50 wt %.

27. The orthopedic device of claim 4, wherein the device is selected from the group consisting of pins, nails, screws, plates and anchors.

28. The orthopedic device of claim 4, wherein the supplemental material is in the form of particulants or fibers.

29. The orthopedic device of claim 28, wherein the supplemental material is present in an amount in the range of about 1–20 wt %.

30. The bone cement of claim 5, wherein the supplemental material is selected to increase compressibility or lead bearing properties of the cement.

31. The bone cement of claim 5, wherein the supplemental material comprises fibers.

32. The bone cement of claim 5, wherein the supplemental material comprises a binder.

* * * * *